United States Patent
Chong

(10) Patent No.: US 11,986,610 B2
(45) Date of Patent: May 21, 2024

(54) NEEDLE ASSEMBLIES AND RELATED METHODS

(71) Applicant: B. Braun Melsungen AG, Melsungen (DE)

(72) Inventor: Meng Mun Chong, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 207 days.

(21) Appl. No.: 16/323,389

(22) PCT Filed: Aug. 18, 2017

(86) PCT No.: PCT/EP2017/070941
§ 371 (c)(1),
(2) Date: Feb. 5, 2019

(87) PCT Pub. No.: WO2018/033628
PCT Pub. Date: Feb. 22, 2018

(65) Prior Publication Data
US 2021/0138200 A1 May 13, 2021

Related U.S. Application Data

(60) Provisional application No. 62/377,307, filed on Aug. 19, 2016.

(51) Int. Cl.
*A61M 25/06* (2006.01)
*A61L 29/08* (2006.01)
(Continued)

(52) U.S. Cl.
CPC ....... *A61M 25/0606* (2013.01); *A61L 29/085* (2013.01); *A61M 25/0014* (2013.01);
(Continued)

(58) Field of Classification Search
CPC .......... A61M 25/0606; A61M 25/0097; A61M 25/0098; A61M 25/005; A61M 25/0054;
(Continued)

(56) References Cited

U.S. PATENT DOCUMENTS 4,046,144 A * 9/1977 McFarlane ........ A61M 25/0606
604/168.01
4,161,177 A * 7/1979 Fuchs ............... A61M 25/0637
D24/112
(Continued)

FOREIGN PATENT DOCUMENTS

EP          0 588 546 A2    3/1994
EP          0588546 A2 * 3/1994 ........ A61M 25/0054
(Continued)

OTHER PUBLICATIONS

Office Action on corresponding foreign application (CN Application No. 201780064923.5) from the National Intellectual Property Administration, P.R. China, dated Nov. 30, 2020.
(Continued)

*Primary Examiner* — William R Carpenter
*Assistant Examiner* — Robert F Allen
(74) *Attorney, Agent, or Firm* — Alumen IP Law PC

(57) ABSTRACT

Aspects of the present disclosure include catheter devices in which a bushing is disposed in an interior cavity of a catheter hub. The bushing has a flexible portion extending out a distal end of the catheter hub. A catheter tube is sleeved over the flexible portion. A needle hub with a needle projects through the flexible portion of the bushing and the catheter tube. The flexible portion is bendable to form at least one curve along the flexible portion. The at least one curve has a minimum bend radius when a first surface of the flexible portion is extended and a second surface opposite the first surface of the flexible portion is shortened.

21 Claims, 10 Drawing Sheets

(51) Int. Cl.
*A61M 25/00* (2006.01)
*A61M 39/24* (2006.01)

(52) U.S. Cl.
CPC .... *A61M 25/0043* (2013.01); *A61M 25/0097* (2013.01); *A61M 39/24* (2013.01); *A61M 2025/0059* (2013.01); *A61M 25/0618* (2013.01); *A61M 25/0693* (2013.01); *A61M 2205/0238* (2013.01)

(58) Field of Classification Search
CPC .. A61M 2025/0059; A61M 2025/0098; A61M 39/10; A61M 25/606; A61M 25/0014; A61M 25/0043; A61M 25/0618; A61M 39/19
See application file for complete search history.

(56) References Cited

U.S. PATENT DOCUMENTS

| | | | |
|---|---|---|---|
| 4,430,083 A * | 2/1984 | Ganz | A61M 25/0045 604/529 |
| 5,330,449 A | 7/1994 | Prichard et al. | |
| 5,380,301 A | 1/1995 | Prichard et al. | |
| 5,466,230 A | 11/1995 | Davila | |
| 2006/0189896 A1 * | 8/2006 | Davis | A61M 25/0043 600/585 |
| 2014/0142509 A1 * | 5/2014 | Bonutti | A61M 25/0662 604/164.03 |
| 2015/0011977 A1 | 1/2015 | Kuniyasu | |
| 2015/0320971 A1 * | 11/2015 | Leeflang | A61L 29/14 427/2.3 |
| 2017/0136217 A1 * | 5/2017 | Riesenberger | A61M 25/0618 |

FOREIGN PATENT DOCUMENTS

| | | | |
|---|---|---|---|
| EP | 588546 A2 * | 3/1994 | ........ A61M 25/0054 |
| JP | H6-210003 A | 8/1994 | |
| JP | 2009-268727 A | 11/2009 | |
| JP | 2011-512895 A | 4/2011 | |
| JP | 2016-509916 A | 4/2016 | |
| WO | WO 95/33507 A1 | 12/1995 | |
| WO | 1999044654 A1 | 9/1999 | |
| WO | WO 2003/099368 A1 | 12/2003 | |
| WO | WO 2009/105484 A2 | 8/2009 | |
| WO | WO 2014/140265 A1 | 9/2014 | |
| WO | WO 2013/146310 A1 | 12/2015 | |

OTHER PUBLICATIONS

International Search Report and Written Opinion on corresponding PCT application (PCT/EP2017/070941) from International Searching Authority (EP) dated Oct. 24, 2017.
International Preliminary Report on Patentability (Chapter I) on corresponding PCT application (PCT/EP2017/070941) from International Searching Authority (EPO) dated Feb. 28, 2019.
Office Action on corresponding foreign application (JP Application No. 2019-509500) from the Japanese Patent Office, dated May 11, 2021.
Examination Report on corresponding foreign application (AU Application No. 2017312325) from IP Australia, dated Oct. 25, 2021.
Office Action on corresponding foreign application (CN Application No. 201780064923.5) from the Chinese Patent Office, dated Oct. 20, 2021.
Examination Report on corresponding foreign application (AU Application No. 2017312325) from IP Australia, dated Jan. 28, 2022.
Examination Report on corresponding foreign application (AU Application No. 2017312325) from IP Australia, dated Jun. 27, 2022.
Office Action on corresponding foreign application (CN Application No. 201780064923.5) from China National Intellectual Property Administration, dated Jul. 6, 2022.

* cited by examiner

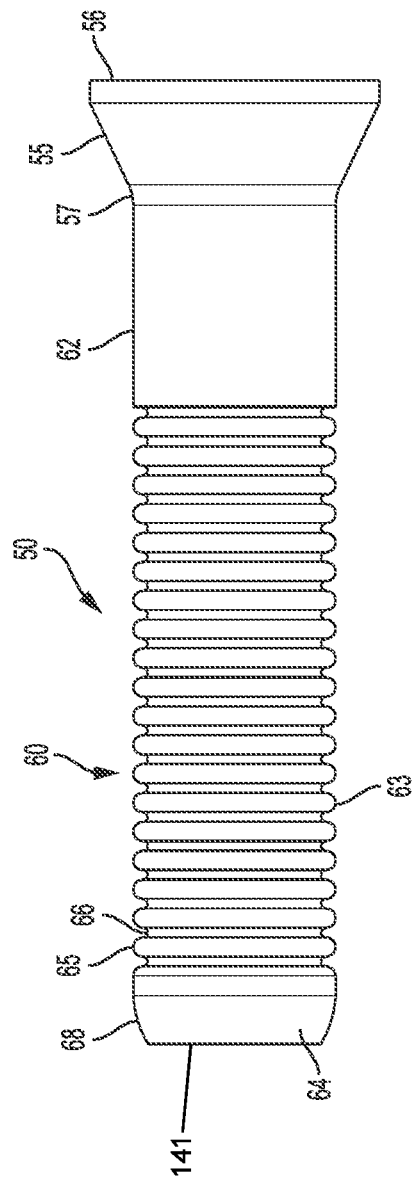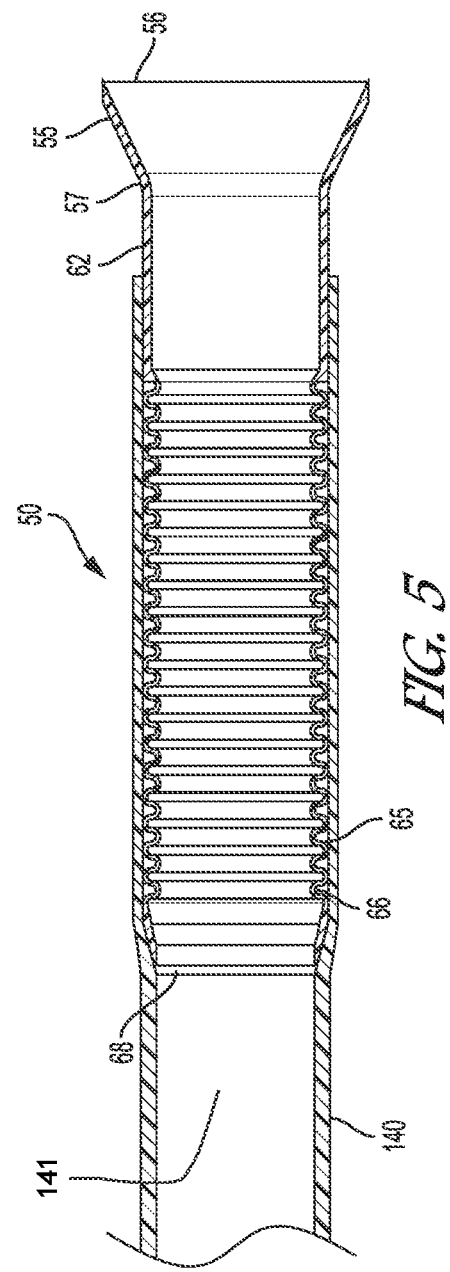

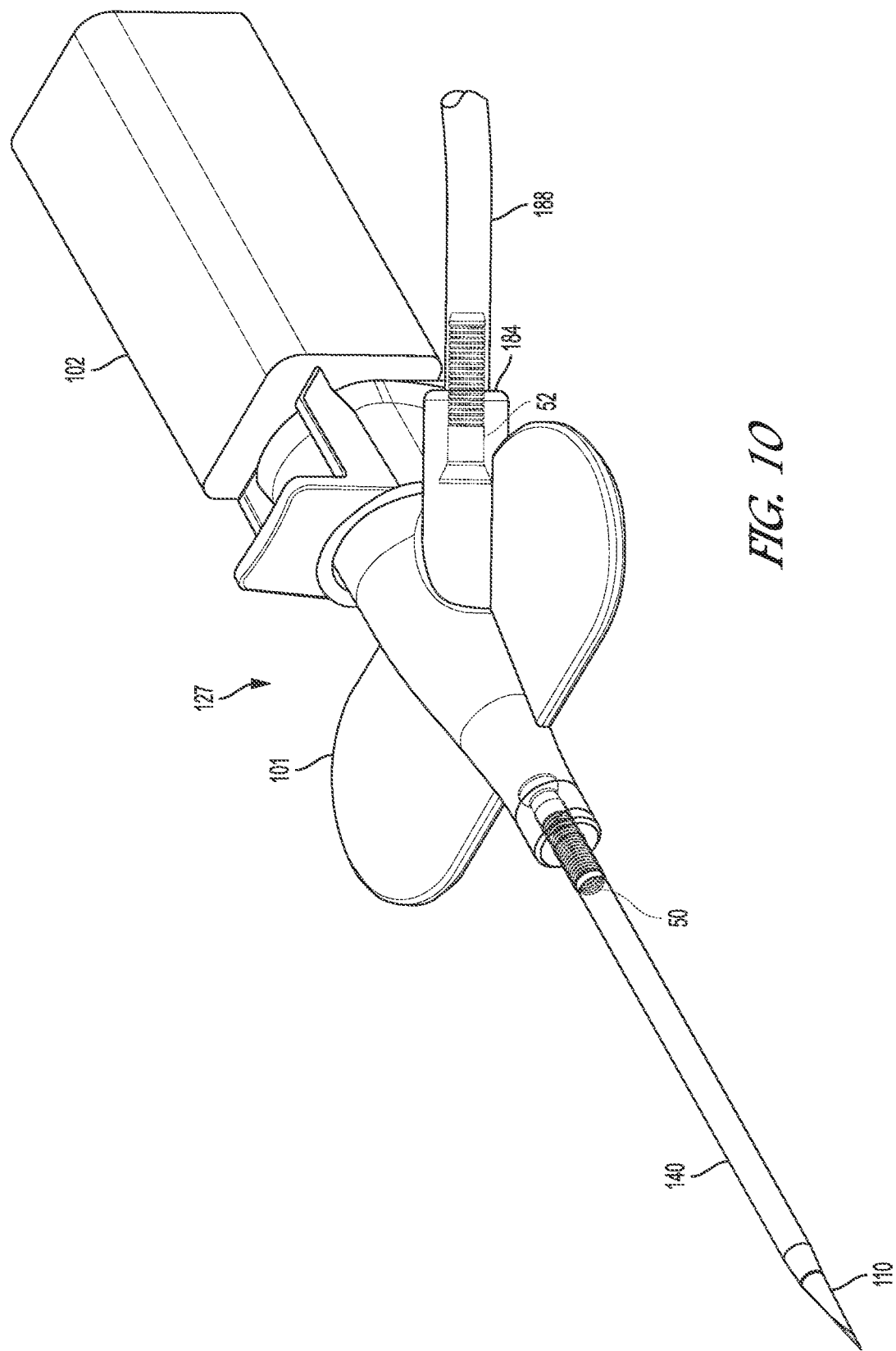

NEEDLE ASSEMBLIES AND RELATED METHODS

FIELD OF ART

The invention relates generally to needle devices, systems, and methods for use where medicines are delivered vascularly. More particularly, the present disclosure relates to catheter devices or assemblies and needle configurations used in intravenous medical devices and methods for using and making such devices and systems.

BACKGROUND

Generally, vascular access devices are used for communicating fluids with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter tube is mounted over an introducer needle having a sharp distal tip. At least the inner surface of the distal portion of the catheter tube tightly wraps or surrounds the outer surface of the needle to prevent peel-back of the catheter tube during insertion of the catheter into the blood vessel. The catheter tube and the introducer needle are assembled so that the needle tip of the introducer needle extends beyond the distal tip of the catheter tube with the bevel of the needle facing up away from the patient's skin. The catheter material can be partially transparent and can have stripes of transparent material and opaque stripes for providing x-ray contrast. The catheter and introducer needle are generally inserted at a shallow angle through the patient's skin into a blood vessel.

In order to verify proper placement of the needle and catheter in the blood vessel, the clinician generally looks for blood flashback as confirmation of the access. The first blood flashback is through the needle and into a transparent needle hub, which is sometimes referred to as primary blood flashback. This confirms at least the needle has found the vein. Then as the needle is withdrawn in a proximal direction away from the catheter tube, the blood will flash back between the needle and the catheter tube. This is sometimes referred to as secondary flashback, which confirms that the catheter tube has found the vein. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the catheter and possibly leaking out the catheter hub.

In some IV catheter assemblies, the needle has an open notch, through which blood can flow into the space between the needle and catheter tube. This "instant flash" confirms only that the needle tip has entered the vein but not necessarily that the catheter tube has entered the vein. Because there is first blood between the needle and the catheter tube when a notch is employed, a secondary flashback is not possible.

The clinician may then withdraw the introducer needle from the catheter. The introducer needle may be withdrawn into a needle tip shield or needle cap that covers the needle tip and prevents accidental needle sticks. When the needle has an open notch, the blood between the distal opening and the open notch is not held by capillary action and can drip from the needle.

After the needle is withdrawn from the catheter, the catheter hub may then be taped against the skin of the patient to firmly secure the catheter hub in place with the catheter tube accessing the blood vessel through an insertion point. Often times, the axis of the catheter tube may not be aligned with and/or is off centered from the centerline of the catheter hub after the catheter hub has been secured to the patient. The difference in alignment between the catheter tube and the centerline of the catheter hub can cause the flexible tube to form a tight bend, which can affect the patient's comfort at the insertion point, restrict flow through the catheter tube at the bend, or form a kink along the catheter tube. Any movement from the patient such as, for example, an extension or flexion of the muscle near the insertion point, can increase discomfort to the patient and can cause a kink to form in the catheter tube.

SUMMARY

The various embodiments of a needle safety assembly have several features, no single one of which is solely responsible for their desirable attributes. Without limiting the scope of the present embodiments as set forth in the claims that follow, their more prominent features now will be discussed briefly.

A catheter device or assembly provided in accordance with aspects of the present disclosure can include a catheter hub having a body defining a hollow interior cavity between a proximal end and a distal end, a bushing, and a catheter tube extending from the bushing.

A needle hub and a needle extending from the needle hub can project through the flexible tube or catheter tube. A needle tip with a needle bevel at a distal end of the needle can extend out a distal end opening of the catheter tube in a ready position. The needle can have a wall surface defining a needle shaft having a needle lumen.

An optional needle shield or needle guard covering the needle tip in a protective position after the needle is withdrawn from the catheter hub following successful venipuncture to prevent needle stick injuries can be secured inside the interior cavity in the ready position. The needle shield can also be provided outside or partially outside the interior cavity. The needle shields can be unitarily formed or can be made separately from multiple parts or components and subsequently assembled together.

The needle can include a change in profile or contour having a different surface contour or shape than the remaining needle shaft. The change in profile can embody a crimp or a radial bulge incorporated near the needle tip for interacting with a perimeter defining an opening on a proximal wall of the needle guard to stop the needle guard from displacing distally off of the needle in the protective position.

Some needle guards can operate without a change in profile on the needle, such as ones that can cant or slant so that an opening that surrounds the needle can grip the needle shaft without a change in profile.

The needle shield can be located in the interior cavity of the catheter hub and have the needle passing therethrough.

The needle shield can be located outside or substantially outside of the catheter hub, such as in a third housing or a guard housing located between the catheter hub and the needle hub.

The catheter tube can be connected to the distal end of the catheter hub via a bushing. The bushing can press a proximal end of the catheter tube between the exterior of the bushing and the interior surface of the catheter hub to retain the catheter tube to the catheter hub.

The bushing can be a bushing that can flex, bend, and/or deform. The bushing can comprise a proximal seat and an elongated seat extending from the proximal seat in a distal direction. The proximal seat can have any shape. For example, the proximal seat can be tapered, non-tapered, have a combination of both tapered and non-tapered features or surfaces, extended, non-extended, regular, or irregular. The elongated seat can be called a distal seat.

The bushing can be secured to the interior cavity of the catheter hub. A part of the distal seat, such as an elongated seat, can extend from the proximal seat and extend out the distal end of the catheter hub. The distal seat can be corrugated or spiraled and can flex and/or bend.

The portion of the distal seat, such as an elongated seat, extending out the distal end of the catheter hub can bend with the catheter tube to deter kinking or collapsing of the catheter tube against a distal end of the elongated seat, as further discussed below.

A bushing in accordance with aspects of the present disclosure can include a proximal seat and a distal seat. The proximal seat can secure a proximal end of a catheter tube to a catheter hub. The distal seat can also secure part of the catheter tube to the catheter hub and can flex to prevent kinking of the catheter tube. The distal seat can have a non-uniform or non-smooth exterior surface. The non-uniform surface can be a corrugated surface, a spiral surface, or both.

The bushing can resemble a funnel, which has a tapered section and an elongated nipple extending from the tapered section. The tapered section, similar to the tapered seat, has a body with wall surfaces that are tapered relative to a lengthwise axis of the elongated nipple.

Alternatively, the bushing can resemble a tube with a non-tapered section and an elongated nipple extending from the non-tapered section. The non-tapered section, similar to the non-tapered seat, can have a body with wall surfaces that are substantially parallel to a lengthwise axis of the elongated nipple.

In some examples, the non-tapered seat and non-tapered section may have a slight draft angle but much smaller or gradual than the tapered angle of the tapered seat. The proximal seat can embody the non-tapered seat.

The needle can extend from a distal end of the needle hub and pass through the interior cavity of the catheter hub through the proximal seat and the elongated seat of the bushing and into the catheter tube with the needle tip extending out a distal end of the catheter tube in the ready to use position.

The distal portion of the catheter tube can be tapered inwardly or have an opening that has a size smaller than an outer diameter of the needle to form a seal around the opening of the catheter tube with the needle to prevent fluid from entering the space between the catheter tube and the needle when the needle tip pierces the skin of a patient at an incision or insertion point. The space between the needle and the interior of the catheter tube can be annular or can be sectioned by baffles, such as ridges.

Blood entering the needle hub can be collected in a vent plug or a blood collection device for sampling. Retraction of the needle tip in a proximal direction into the catheter tube can allow fluid or blood to flow into the space between the needle and the interior of the catheter tube.

The catheter hub assembly can include a catheter hub, a catheter tube, and a bushing located in the interior of the catheter hub with part of the elongated seat extending distally out the distal end of the catheter hub.

The part of the elongated seat that extends out the distal end of the catheter hub can be flexible, such as capable of bending or bowing.

The catheter hub can have an interior cavity defined between an opening at a proximal end of the catheter hub and an opening at a distal end of the catheter hub. The bushing can be inserted through the opening at the proximal end of the catheter hub and secured at a distal end of the interior cavity of the catheter hub via press fit, interference fit, adhesive, combinations thereof, or other fastening means.

The bushing can include a proximal seat, such as a tapered seat, a non-tapered seat, or combinations thereof, and an elongated seat extending from the proximal seat.

The proximal seat, which can be a tapered seat, a non-tapered seat, or combinations thereof, and the elongated seat can be integrally formed.

In some examples, the non-tapered seat may have one or more portions with a slight draft angle but much smaller or gradual than the tapered angle of the tapered seat.

The embodiment of the bushing with a proximal seat, which can have a non-tapered seat, can be used with a correspondingly shaped nose section of a needle hub to attach a proximal end of a catheter tube to the catheter hub. In an example, the non-tapered seat of the bushing is positioned in a bore of a nose section of a catheter hub and wedging a catheter tube against the interior wall surface of the bore and the exterior of the proximal seat.

Alternatively, the tapered or non-tapered seat and the elongated seat may be formed as separate pieces that are assembled together by welding or other fastening means. The choice of material of the bushing is of the type that can withstand temperature fluctuations, impacts, corrosive substances, heat, and the atmosphere.

The bushing can be metallic or plastic, or a combination of materials.

A hydrophobic coating can be applied to at least portions of the inner and outer surfaces of the bushing to prevent thrombus formation, phlebitis, or blood clots.

A parylene coating can be applied to at least the inside surface of the elongated seat portion to prevent thrombus formation.

The tapered seat can be conical or funnel shaped having a defined thickness with a body having a wider opening at a proximal end and a relatively narrower opening at the distal end of the funnel body. The narrower opening can transition to the elongated seat.

The non-tapered seat can be cylindrical and have a same diameter as the elongated seat. Alternatively, the non-tapered seat can have a different diameter than the elongated seat. The non-tapered seat can be rigid and inflexible or semi-rigid.

The proximal seat, which can have a tapered seat, a non-tapered seat, or combinations thereof, can have slots to facilitate flexing and assembly of the bushing into the nose section of the catheter hub. The slots can be parallel to the lengthwise axis of the catheter hub. The slots can be spaced apart from one another.

The tapered seat can be rigid and inflexible or semi-rigid to maintain its conical shape after insertion into the catheter hub to thereby wedge the proximal end of the catheter tube to the interior of the catheter hub.

Alternatively, proximal seat, which can include a tapered or non-tapered seat, can be flexible and elastic. The proximal seat, such as a tapered or a non-tapered seat, can be secured inside the interior cavity of the catheter hub by interference fit or by using fastening means, such as recessed surfaces, bumps, shoulders, washing or retaining nut, etc.

A retaining mechanism or retainer may be provided inside the catheter hub to secure the tapered or non-tapered seat inside the interior cavity.

The bushing can be inserted into the interior cavity of the catheter hub from the opening at the proximal end of the catheter hub and pushed distally until the tapered or non-tapered seat slides over the retainer and snaps into a securing position between the distal end of the catheter hub and the retainer.

The retainer can be a raised circumferential ring or shoulder formed inside the interior cavity of the catheter hub for the proximal end of the tapered or non-tapered seat to rest against.

The raised circumferential ring or shoulder can have a bore diameter smaller or slightly smaller than a diameter of the wider opening at the proximal end of the tapered or non-tapered seat to provide a positive engagement for the tapered or non-tapered seat and prevent the tapered or non-tapered seat from sliding proximally out after snapping into position.

The circumferential ring can taper gradually inward distally to assist sliding the bushing into the securing position.

The circumferential ring can have a recess or other surface features to resist the distal end of the tapered or non-tapered seat and prevent the bushing from sliding proximally out the interior cavity.

The retainer may be a series of bumps or protrusions.

The elongated seat of the bushing can be cylindrical and extends from the narrow opening at the distal end of the tapered or non-tapered seat.

The elongated seat can have a smooth portion transitioning from the distal end of the tapered or non-tapered seat, a less smooth portion, and a distal end, which can be smooth with a taper as shown or can have a roughened surface.

The smooth portion can have an exterior surface appearance that is generally flat or has fewer surface roughness than the less smooth portion.

The less smooth portion can be a flexible portion formed distally of the smooth portion of the elongated seat.

The smooth portion can be omitted, in which case, the elongated seat includes only the less smooth portion extending from the tapered or non-tapered seat.

The less smooth or flexible portion can be deformed or bend more readily than the smooth portion. The smooth portion and the tapered or non-tapered seat can be rigid and inflexible or semi-rigid with some flexibility.

The flexible portion can be flexible and can bend along a length of the flexible portion to form a bend, a curve, or a bow along the length of the flexible portion.

The flexible portion can be compressed to form a shorter flexible portion, or pulled, such as stretch, to form a longer flexible portion.

The flexible portion can have a number of alternating ridges and grooves.

The smooth portion can be without any alternating grooves and ridges.

The alternating ridges and grooves of the flexible portion can be rounded along the peaks and valleys to form a corrugated tube structure with a corrugated profile.

The alternating ridges and grooves may be folded upon each other to form an accordion like structure.

A combination of folded and rounded ridges and grooves can form the flexible portion.

The corrugated tube structure can allow the elongated seat to move, flex, bow, and/or bend to adjust the flexible portion for alignment, for use when a catheter tube is inserted into a patient, for securement, or any number of reasons.

The corrugated structure can also absorb movement and vibration.

The alternating ridges and grooves can allow the flexible portion to bend and form one or more curves or bows along the length of the flexible portion.

The flexible portion of the elongated seat can be manipulated from an initial straight configuration to a new configuration with one or more bends, with compressed portions, and/or stretched portions.

The flexible portion can remain in its current configuration without elastically returning back to its original configuration, the flexible portion can be elastic, in which the flexible portion can spring back or return to its original shape after the deformation, or the flexible portion can be freely manipulated but cannot maintain the new configuration or return to its original shape.

The corrugated tube structure can convey liquids and gases under pressure in the operating conditions of the catheter assembly.

A hydrophobic coating can be applied to the bushing to form a surface layer on the inside of the elongated seat to repel blood and prevent thrombus formation or blood clotting from blood collecting on the corrugated profile surface.

The elongated seat can be inserted into the catheter tube so that the flexible portion is inside the catheter tube and the proximal end of the catheter tube is located at the smooth portion. The catheter tube can extend to the tapered or non-tapered seat, or at least part of the way thereof.

The insertion end of the elongated seat may be tapered and may be provided at a free end of the flexible portion to aid assembling of the elongated seat into the catheter tube.

A seal can form at the interface between the lumen of the catheter tube and the bushing such that fluid cannot flow therebetween.

A diameter of the elongated seat can be the same or larger than the diameter of the lumen of the catheter tube. Thus, the catheter tube can be stretched over the elongated seat to form a tight secure fit.

Adhesive or other fixing means can be provided to further secure the catheter tube to the elongated seat and/or the tapered or non-tapered seat.

The flexible portion can bend to form an elbow. If the flexible portion is long enough, more than one elbow can form. The elbow can form when one of the corrugated surfaces, such as the inside radius of the elongated seat, is shortened while the opposite surface, such as the outside radius of the elongated seat, is extended.

A bend radius of the elbow can depend on the diameter of the flexible portion and the geometry and size of the ridges and grooves, such as for example, the width of the ridges and the width of the grooves, which can determine the number of ridges and grooves for a given length of the flexible portion.

The smallest bend radius of the elbow can occur when the ridges are contacting each other along the interior of the elbow and farthest away from each other along the exterior of the elbow.

The maximum bend angle of the bushing can be realized at the smallest bend radius of the elbow.

The catheter tube can be attached to the elongated seat of the bushing.

The catheter tube can be sleeved onto the elongated seat to surround at least the flexible portion of the elongated seat to prevent the catheter tube from kinking or collapsing within the flexible portion.

The catheter tube may also sleeve over the smooth portion if the smooth portion is present.

The catheter tube can bend with the elbow along the flexible portion to prevent the catheter tube from kinking, collapsing, or restricting flow even if the catheter tube bends, such as during securement of the catheter assembly, due to inadvertent movement, etc. Thus, the flexible portion can impart flexibility on the catheter tube while maintaining flow through the catheter tube and catheter hub.

The flexible portion can impart flexibility to the catheter tube and prevent kinking to the catheter tube at a location externally of the catheter hub while maintaining flow through the catheter tube and catheter hub.

The smooth portion can be rigid and not bend.

The elbow can also maintain the bent configuration of the catheter tube by reducing or eliminating any restoration forces by a normally bent catheter tube. That is, any deviation of the catheter tube from the axis of the catheter hub can be imparted to the flexible portion of the elongated seat instead of the insertion point of the catheter tube to reduce patient discomfort.

Occurrence of phlebitis due to the movement of the catheter tube at the insertion point can be reduced.

The distal end of the catheter hub can have a radiused opening forming a recess to accommodate flexing of the catheter tube and the flexible portion of the elongated seat at a location external of the catheter hub.

The shape of the recess is not limited and can embody any shape provided sufficient clearance is provided to accommodate movement of the catheter tube and the flexible portion at a location external of the catheter hub, such as distal of the distal end.

The recess may allow the catheter tube to bend with the flexible portion of the bushing inside the recess. The recess can be sized to restrict or allow the maximum bend of the flexible portion with the catheter tube.

A flexible portion of the elongated seat of the bushing can have a continuous ridge spiraling continuously around the length of the flexible portion from one end of the flexible portion to the other end of the flexible portion to form a spiral corrugated tube structure rather than alternating ridges and grooves along the length of the flexible portion.

Thus, the present bushing can be understood to include a helical shaped ridge extending from one end of the flexible portion to another end of the flexible portion.

The bushing can include a tapered seat and an elongated seat extending from the tapered seat.

The elongated seat can include the flexible portion and an optional smooth portion extending between the tapered seat and the elongated seat.

An insertion end with a taper can be provided at the distal end of the flexible portion to assist sleeving the catheter tube over the elongated seat of the bushing.

A seal may be formed between the lumen of the catheter tube and the bushing.

The bushing can be bent along the flexible portion to form one or more bends or elbows.

The bend radius of the elbow can depend on the geometry and size of the continuous ridge and the groove. When bending, a portion of one side of the flexible portion will be shortened, and another portion at the opposite side will be extended.

The bushing can include a proximal seat, such as a non-tapered seat, and an elongated seat extending from the non-tapered seat. The elongated seat can include a flexible portion and an optional smooth portion extending between the proximal seat and the elongated seat.

The flexible portion of the elongated seat of the bushing can have alternating ridges and grooves along the length of the flexible portion to form a corrugated structure or a continuous ridge spiraling continuously around the length of the flexible portion from one end of the flexible portion to the other end of the flexible portion to form a spiral corrugated tube structure.

Thus, the present bushing can be understood to include a helical shaped ridge extending from one end of the flexible portion to another end of the flexible portion or alternating ridges and grooves along the length of the flexible portion. The helical shaped ridge can extend from a proximal seat.

The non-tapered seat can be cylindrical and have substantially the same diameter as the smooth portion, such that the smooth portion and the non-tapered seat are one and the same.

The bushing can be secured inside the catheter hub using glue, interference fit, or other securing means to prevent the bushing from moving distally out the catheter hub or into the catheter tube.

Alternatively, the non-tapered seat can have a different diameter, shape, or size than the smooth portion.

An insertion end with a taper can be provided at the distal end of the flexible portion to assist sleeving the catheter tube over the elongated seat of the bushing.

A seal may be formed between the lumen of the catheter tube and the bushing.

The bushing can be bent along the flexible portion to form one or more bends or elbows.

The bend radius of the elbow can depend on the geometry and size of the continuous ridge and the groove. When bending, a portion of one side of the flexible portion may be shortened, and another portion at the opposite side may be extended.

The bushings can be formed by applying a deep drawing process followed by a hydroforming process to produce the corrugated surface.

A coating process can be applied to the bushing, such as to the inner surface of the bushing.

A catheter assembly can comprise a catheter hub and a catheter tube attached to one of the bushings so that at least part of the elongated seat extends out a distal end of the catheter hub.

A needle hub having a needle can extend through the catheter tube.

The catheter hub can include side fluid port and a fluid adaptor attached to the side fluid port by a tubing attached to the side fluid port by a second bushing. A part of the elongated seat of the second bushing can extend out from or externally of the side fluid port.

The second bushing can have a cylindrical seat. To prevent the second bushing from being pulled out of the catheter hub, the second bushing can be secured to the catheter hub with glue, interference fit, other securing means, or a combination thereof.

The tubing can have a lumen for fluid flow between the side fluid port and the fluid adaptor, which can be a needleless female Luer adaptor.

The two bushings can each form one or more bends or elbows along a flexible portion of the respective bushing.

The flexible portions of the two bushings can bend at or within the catheter hub or side fluid port, near the respective opening thereof, and at a location external to the catheter hub or the side fluid port.

Portions of the tubing and the catheter tube sleeved on the flexible portion of the respective bushing can also bend along the flexible portion.

The proximal end of the catheter hub can be equipped with a septum, a seal or a valve, which can prevent flow thereacross after removal of the needle and the needle hub.

A needle guard can be incorporated between the needle hub and the catheter hub.

The catheter hub can have a pair of wings.

The needle hub can alternatively have a wing that extends distally along a side of the catheter hub opposite the side fluid port.

A needle tip of the needle can extend distally past a distal opening of the catheter tube.

Fluid can be infused through the fluid adaptor via the tubing to the side port and then to the catheter hub.

If the proximal end of the catheter hub has a valve instead of a septum or a seal, then fluid can be infused through the valve and the catheter tube. A clamp (not shown) can also be used to clamp off the extension line between the side fluid port and the fluid adapter.

The catheter assembly can include a valve activator or actuator for opening a valve, which can have one or more slits defining a plurality of flaps that can be opened when the activator is advanced by a male medical implement, such as a syringe tip, male Luer connector, or a Luer adaptor.

The actuator can have a nose section for physically opening the valve and a plunger end comprising at least one plunger element or leg configured to be pushed by a male medical implement.

The valve, valve actuator, and needle guard can be omitted.

The valve can be housed within the interior cavity of the catheter hub and when incorporated has the needle projecting therethrough in the ready position.

Three slits can be provided on the valve forming three flaps. Four slits in the shape of an "X" can be provided to form four flaps. Different number of slits and flaps can be contemplated.

The valve can be seated in a valve seat formed in the interior cavity of the catheter hub.

An undercut can be formed in the interior of the catheter hub to retain the valve inside the interior cavity.

Bumps or protrusions can be provided around an exterior of the valve to create paths between the valve and the interior of the catheter hub for venting during blood flashback.

When the needle is withdrawn from the catheter hub after placement of the flexible tube in the patient's vasculature, the one or more slit can close such that the valve seals upon itself thereby restricting or limiting flow across the valve.

The valve can thus restricts back bleed through the catheter hub.

The valve can be constructed of a material that forms a seal or a restriction at the interface with the needle and reseals after the needle is withdrawn.

The valve can comprise silicone, silicone rubber, polypropylene, or other suitable materials.

The activator can be provided to press against the valve, such as to project through the slits to open or deflect the flaps, when moved distally by a medical implement to open the valve to allow fluid or solution to pass through the valve.

The activator can have a passage formed through the nose section for receiving the needle in the ready position and for fluid flow when the catheter hub is connected to an IV line.

The activator can have surface features to provide fluid mixing as fluid enters the catheter hub.

After the needle and needle hub are removed, a male medical implement, such as a Luer tip of a syringe, a male Luer connector or adaptor, such as used in connection with an IV line, a Luer access connector, or a vent plug, can be inserted to push the activator distally into the seal to open the seal.

The activator can be advanced distally by a syringe tip, which can press against the proximal end of a disc of the valve by the activator to push a nose section of the activator distally forward into the valve inside the skirt to open the one or more slits.

The activator can have a wedge shaped nose section to press open the valve and one or more extensions, plungers, or legs extending in a proximal direction from the nose section to be pushed against by a male medical implement.

The extension can embody one or more separate sections that can be pressed against by a male medical implement to advance the activator against the valve.

Two spaced apart extensions can be provided to accommodate a needle guard therebetween.

A disc and a skirt can be positioned in a seam of a two-piece catheter body.

The needle shield can be supported or housed in an intermediate hub between the catheter hub and the needle hub.

The intermediate hub can be removably coupled with the catheter hub and may be referred to as a third hub or a needle shield or needle guard housing.

The catheter hub can be provided with a valve that can be actuated with fluid pressure only so that the actuator may be omitted from inside the interior cavity of the catheter hub.

The valve can flex with head pressure from an IV bag hung on an IV pole pushing up against the valve to open one or more flow paths or channels for fluid flow.

The valve can be positioned closed to the proximal opening of the catheter hub to be opened by a male Luer connected to the proximal open end of the catheter hub without the actuator or activator.

Part of the elongated seat of the bushing extending out a distal end of the catheter hub can form one or more bends or elbows along a flexible portion of the bushing.

The flexible portion can bend at, within the catheter hub, and/or external of the catheter hub. Portions of the catheter tube sleeved on the flexible portion can also bend along the flexible portion.

A safety catheter assembly can include a needle safety shield or needle guard, which comprises a biasing or resilient member, such as a resilient arm, completely outside or substantially outside of the catheter hub.

An intermediate hub, a needle shield hub, or a third hub can be located, at least in part, between the catheter hub and the needle hub.

The needle can have a change in in profile or contour.

The needle shield can be located on or in the intermediate hub.

The intermediate hub can have a single wall, or can have openings in the wall.

The needle shield can be supported by a sleeve of the intermediate hub or can have the distal arms directly touching the needle.

The sleeve can extend from a distal wall of the intermediate hub so that the resilient arms of the needle safety shield are supported on the sleeve.

The needle can incorporate a change in profile associated with a flashback indicator or on a cover applied over the flashback indicator, such as a projection, for engaging an opening on the proximal wall of the needle shield.

The change in contour or profile can engage the proximal wall of the needle shield and pull the needle shield proximally so that the two resilient arms are pulled off the sleeve or no longer biasing against the needle and can overlap to block the needle tip.

The bushing extending out a distal end of the catheter hub can form one or more bends or elbows along a flexible portion of the bushing.

The flexible portion can bend at, within the catheter hub, or external of the catheter hub. Portions of the catheter tube sleeved on the flexible portion can also bend along the flexible portion.

Aspects of the present disclosure include a catheter device or assembly, which can include a catheter hub having an interior cavity, a bushing disposed in the interior cavity and having a flexible portion extending out a distal end of the catheter hub, a catheter tube sleeved over the flexible portion.

The catheter device can further include a needle hub with a needle comprising a wall surface defining a needle shaft having a needle lumen and a needle tip projecting through the flexible portion of the bushing and the catheter tube.

An elongated seat of a bushing can have a flexible portion. The bushing and/or the flexible portion can have a lengthwise direction or axis.

The flexible portion can be bendable to form at least one curve along the flexible portion to prevent kinking in the catheter tube. The at least one curve can have a minimum bend radius when a first surface of the flexible portion is extended and a second surface opposite the first surface of the flexible portion is shortened.

A bend radius of the at least one curve can define an elbow. The radial curve of the elbow can depend on the diameter of the flexible portion and the geometry and size of the ridges and grooves of the flexible portion. For example, the width of the ridges and the width of the grooves along a length of a flexible portion can determine the number of ridges and grooves for the given length of the flexible portion. The smallest bend radius of the elbow can occur when the ridges are contacting each other along the interior of the elbow and farthest away from each other along the exterior of the elbow at the surface of the elbow.

If an imaginary plane bisects the bushing, such as the diameter of the elongated seat of the bushing along the lengthwise direction of the bushing, to divide the bushing into two halves, which can be called a first bushing half and a second bushing half, then the smallest bend radius of the elbow can occur when the ridges are contacting each other, or the gaps or spacing can shortened but not touch, along the interior of the first bushing half and farthest or further away from each other along the exterior of the second bushing half.

The reference to first bushing half and second bushing half are to distinguish between two sections of the elongate seat only but not structurally limiting. Thus, it can also be said then that the largest bend radius of the elbow can occur when the ridges are extended from each other along the exterior of the first bushing half and shortened or being closer together along the interior of the second bushing half Said another way, the at least one curve can have a minimum bend radius when a first surface of the first bushing half of the elongated seat is extended and a second surface of the second bushing half of the elongated seat is shortened.

As the flexible portion of the bushing can bend in any number of locations and bending directions depending on the force applied to the catheter tube and/or the bushing to cause the bending and to cause at least one curve on the bushing, different opposed surfaces of the bushing can undergo changes, such as deformation, stretching, compressing, etc., to result in different parts of the bushing being called a first bushing half and a second bushing half depending on the direction of the bend.

Thus, a catheter assembly of the present disclosure can comprise a catheter hub having a hub body defining an interior cavity; a bushing disposed at least in part in the interior cavity and having an elongated seat having a portion extending out a distal end of the catheter hub, said elongated seat comprising a first bushing half and a second bushing half located on different sides of a plane extending lengthwise of a diameter of the bushing; a catheter tube sleeved over the elongated seat including over the portion that extends out the distal end of the catheter hub or sleeved into a distal opening at a distal end of the elongated seat; a needle hub with a needle comprising a needle shaft having a needle lumen and a needle tip, the needle shaft projecting through the elongated seat of the bushing and the catheter tube in a ready to use position.

In some examples, the elongated seat is bendable to form at least one curve along a length thereof to prevent kinking in the catheter tube, the at least one curve having a minimum bend radius when a first surface of the first bushing half of the elongated seat is extended and a second surface of the second bushing half of the elongated seat is shortened.

The flexible portion can form a corrugated tube structure having alternating ridges and grooves. The alternating ridges and grooves are rounded to form a corrugated profile surface. Alternatively, the alternating ridges and grooves can be folded upon each other to form an accordion structure. In other embodiments, a combination of folded and rounded ridges and grooves can form the flexible portion.

The flexible portion can bend to form one or more bends along the flexible portion. A minimum bend radius of the one or more bends can be achieved when alternating ridges at a first surface of the flexible portion are extended further from each other and alternating ridges at a second surface of the flexible portion, opposite the first surface, are contacting each other.

A hydrophobic coating layer can also be formed on an inside surface of the flexible portion. The hydrophobic coating layer can be a parylene coating layer. The parylene coating later can prevent blood from collecting inside the flexible portion to prevent phlebitis or thrombus formation.

The flexible portion may also form a spiral corrugated tube structure having a continuous ridge spiraling continuously around the flexible portion from one end of the flexible portion to the other end of the flexible portion. The minimum bend radius of the flexible portion having the spiral corrugated tube structure can be achieved when adjacent portions of the ridge at a first surface of the flexible portion are extended further from each other and adjacent portions of the ridge at a second surface of the flexible portion are touching, in which the first surface is opposite the second surface. A hydrophobic coating layer can also be formed on an inside surface of the flexible portion. The hydrophobic coating layer can be a parylene coating layer.

The bushing can further comprise a tapered or non-tapered seat coupled to the flexible portion. The tapered or non-tapered seat can be integrally formed with the flexible portion. The tapered or non-tapered seat being conical with a wider opening at a proximal end and a narrower opening at a distal end.

A smooth portion can be coupled between the tapered or non-tapered seat and the flexible portion. That is, the smooth portion can extend from the distal end of the tapered or non-tapered seat. The smooth portion can be more rigid than the flexible portion. A tapered portion can extend from a distal end of the flexible portion.

The bushing can be metallic. Alternatively, the bushing can be plastic.

A retainer can be formed inside the interior cavity of the catheter hub to secure the tapered or non-tapered seat of the bushing inside the interior cavity. The retainer can be a circumferential ring protruding from a surface of the interior cavity having a bore diameter smaller than a diameter of the tapered or non-tapered seat.

A recess can be defined in the distal end of the catheter hub. The shaped of the recess can be frustoconical shaped. The shape of the recess is not limited and can be other shapes such as a cylindrical shape.

A valve and an activator can be located in the interior cavity of the catheter hub proximal of the valve. The activator can be configured to press open the valve. The activator can comprise at least one plunger element configured to be pushed by a male Luer tip.

A needle shield can be provided to cover the needle tip. The needle shield can be located substantially in the interior cavity of the catheter hub or in an intermediate hub proximal of the catheter hub.

A side port can be formed with the catheter hub, with another bushing having a flexible portion extending out a distal end of the side port. Thus the catheter hub with the side port can have two bushings extending out the distal end of the catheter hub and the side port. A catheter tube can be attached to the flexible portion of the bushing extending out the distal end of the catheter hub and the tubing can be attached to the flexible portion of the other bushing extending out the side port. A fluid adaptor can be attached to the free end of the tubing.

Another aspect of the present disclosure includes a method for manufacturing a catheter assembly. The method can include forming a catheter hub having an interior cavity, and a bushing.

The bushing can be formed by a deep drawing process. A hydroforming process can be applied to produce a corrugated surface on a flexible portion of the bushing.

The catheter tube can then be sleeved over the flexible portion. The bushing with the catheter tube can be secured in the interior cavity of the catheter hub, with the flexible portion extending out a distal end of the catheter hub.

A needle hub with a needle comprising a wall surface defining a needle shaft having a needle lumen and a needle tip can be formed. The needle can project through the flexible portion of the bushing and the catheter tube.

The flexible portion can be bendable to form at least one curve along the flexible portion to prevent kinking in the catheter tube. The at least one curve can have a minimum bend radius when a first surface of the flexible portion is extended and a second surface opposite the first surface of the flexible portion can be shortened.

The method can further include coating the inner surface of the flexible portion of the bushing to form a hydrophobic coating layer.

The method can also include placing a needle guard having a proximal wall with a proximal opening and two resilient arms slidably on the needle shaft.

A valve can be used to limit fluid flow through a catheter hub with an actuator in dynamic contact with the valve.

An alternative embodiment includes placing the catheter tube inside the elongated seat and then securing the catheter tube to the bushing.

In an example, the bushing is made from a metal material or from a polymer or polymer matrix material. The catheter tube can be inserted into the distal opening, such as being sleeved into the bushing, at the distal end of the elongated seat.

In an example, the proximal end of the catheter tube is inserted to a location along the less smooth portion of the elongated seat. In another example, the proximal end of the catheter tube is inserted to a location along the smooth portion of the elongated seat. Ultrasonic welding can then be used to weld the catheter tube to the bushing using a modified sonotrode, which is understood to be a tool that creates ultrasonic vibrations.

Another alternative embodiment includes placing the catheter tube inside the elongated seat of the bushing and then securing the catheter tube to the bushing by adhesive or gluing. In an example, glue is applied, such as sprayed, dipped, or coated onto the inner surface of the elongated seat.

The proximal end of the catheter tube can then be inserted into the distal opening at the distal end of the elongated seat. The adhesive or glue may be air dried or dried with the aid of heat activation.

Thus, as described, the catheter tube can be sleeved over the bushing or into the bushing. For example, the catheter tube can be sleeved over the elongated seat or into the elongated seat.

The elbow, curve, bend, and bow, such as when the flexible portion of the bushing is moved, can be understood as being a synonymous structure and results from movement of the bushing. The elbow, curve, bend, or bow is a structure that is not substantially linear, as in a bushing with a straight or linear nose section.

An aspect of the present disclosure can include a catheter assembly comprising: a catheter hub having a hub body defining an interior cavity; a bushing disposed at least in part in the interior cavity and having an elongated seat having a portion extending out a distal end of the catheter hub; a catheter tube sleeved over the elongated seat including over the portion that extends out the distal end of the catheter hub or sleeved into a distal opening at a distal end of the elongated seat; a needle hub with a needle comprising a needle shaft having a needle lumen and a needle tip, the needle shaft projecting through the elongated seat of the bushing and the catheter tube in a ready to use position; and wherein the elongated seat is bendable to form at least one curve along a length thereof to prevent kinking in the catheter tube, the at least one curve having a minimum bend radius when a first surface of the elongated seat is extended and a second surface opposite the first surface of the elongated seat is shortened.

A method for manufacturing a catheter assembly can comprise: forming a catheter hub with an interior cavity; sleeving a catheter tube over a corrugated surface on an elongated seat of a bushing or into the elongated seat of the bushing; securing the bushing in the interior cavity of the catheter hub; extending a portion of the corrugated surface out a distal end of the catheter hub; forming a needle hub with a needle comprising a needle shaft a needle lumen and a needle tip, the needle shaft projecting through the elongated seat of the bushing and the catheter tube; and wherein the elongated seat is bendable to form at least one curve to prevent kinking of the catheter tube, the at least one curve having a minimum bend radius when a first surface of the elongated seat is extended and a second surface opposite the first surface of the elongated seat is shortened.

BRIEF DESCRIPTION OF THE DRAWINGS

These and other features and advantages of the present devices, systems, and methods will become appreciated as the same becomes better understood with reference to the specification, claims and appended drawings wherein:

FIG. 4 shows an embodiment of a flex bushing provided in accordance with aspects of the present disclosure in a side view;

FIG. 5 shows the flex bushing of FIG. 4 attached to a catheter tube;

FIG. 10 shows another embodiment of a safety IV catheter assembly;

DETAILED DESCRIPTION

The detailed description set forth below in connection with the appended drawings is intended as a description of the presently preferred embodiments of needle assemblies and components for use with or forming the needle assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
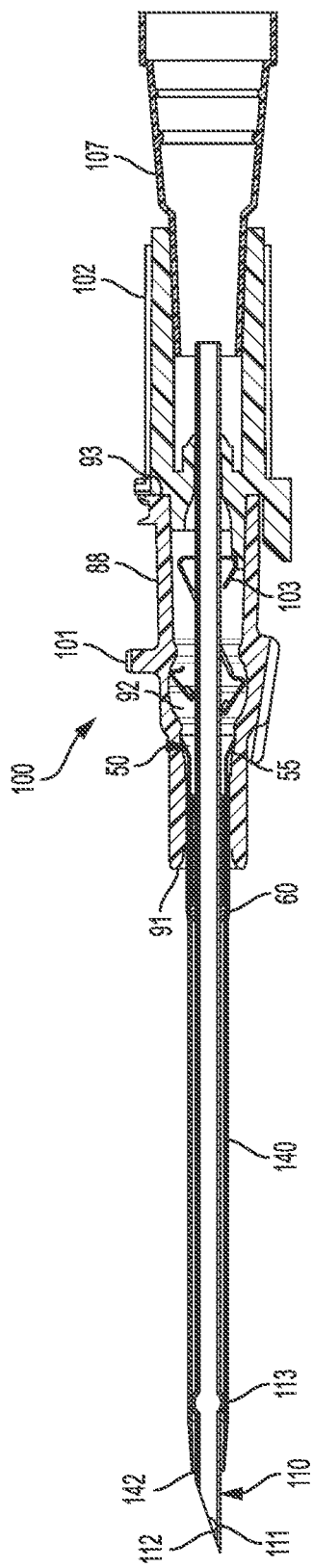
FIG. 1 is a cross sectional view of a safety IV catheter assembly provided in accordance with aspects of the present disclosure.

FIG. 1 shows a catheter device or assembly 100 provided in accordance with aspects of the present disclosure. The catheter device 100 can include a catheter hub 101 having a body 88 defining a hollow interior cavity 92 between a proximal end 93 and a distal end 91, a needle hub 102, and a needle 110 extending from the needle hub 102 and projecting through a flexible tube or catheter tube 140. A needle tip 112 with a needle bevel at a distal end of the needle 110 can extend out a distal end opening 142 of the catheter tube 140 in the ready position of FIG. 1. The needle 110 can be understood to have a wall surface defining a needle shaft 111 having a needle lumen.

The catheter device 100 can optionally include a needle shield or needle guard 103 to cover the needle tip 112 in a protective position after the needle 110 is withdrawn from the catheter hub 101 following successful venipuncture to prevent needle stick injuries. The needle shield can be secured inside the interior cavity 92 in a ready to use position. The needle shield can also be provided outside or partially outside the interior cavity 92, as further discussed below with reference to FIG. 12. Examples of needle shields can be found in U.S. Pat. No. 8,827,965 and in U.S. patent application Ser. No. 13/257,572, published as US 2012/0046620 A1, the contents of which are expressly incorporated herein by reference. These needle shields can be unitarily formed or can be made separately from multiple parts or components and subsequently assembled together.

The needle 110 can include a change in profile or contour 113 having a different surface contour or shape than the remaining needle shaft. The change in profile 113 can embody a crimp or a radial bulge incorporated near the needle tip 112 for interacting with a perimeter defining an opening on a proximal wall of the needle guard 103 to stop the needle guard 103 from displacing distally off of the needle 110 in the protective position. Some needle guards 103 can operate without a change in profile 113 on the needle 110, such as ones that can cant or slant so that an opening that surrounds the needle can grip the needle shaft without a change in profile. In the embodiment of FIG. 1, the needle shield 103 is located in the interior cavity of the catheter hub 101 and has the needle 110 passing therethrough. In other examples, the needle shield 103 is located outside or substantially outside of the catheter hub, such as in a third housing or a guard housing located between the catheter hub and the needle hub. Optionally the needle guard 103 can be omitted.

The catheter tube 140 can be connected to the distal end of the catheter hub 101 via a bushing 50. The bushing 50 presses a proximal end of the catheter tube 140 between the exterior of the bushing and the interior surface of the catheter hub to retain the catheter tube to the catheter hub. In an alternative embodiment, rather than pinching the proximal end of the catheter tube between the catheter hub and the exterior of the bushing, the catheter tube 140 can be inserted inside the bushing and secured thereto, such as by gluing or by welding the catheter tube and the bushing together, as further discussed below.

In an example, the bushing 50 can be a bushing that can flex, bend, and/or deform. The bushing 50 can comprise an anchor or proximal seat, such as a tapered seat 55 or a non-tapered seat (FIG. 9B), and an elongated seat 60, which can also be called a distal seat, extending from the tapered seat 55 in a distal direction. The shape of the proximal seat is not limited to being tapered or non-tapered. For example, the shape of proximal seat can have a combination of both tapered and non-tapered features, extended, non-extended, regular, or irregular.

In one example and when the bushing 50 is secured to the interior cavity 92 of the catheter hub 101, part of the elongated seat 60 extending from the tapered seat 55 can extend out the distal end 91 of the catheter hub 101. In an example, the portion of the elongated seat 60 extending out the distal end 91 of the catheter hub 101 can bend with the catheter tube 140 to deter kinking or collapsing of the catheter tube 140 against a distal end of the elongated seat 60, as further discussed below. The bushing 50 can resemble a funnel, which has a tapered section and an elongated nipple extending from the tapered section. The tapered section, similar to the tapered seat 55, has a body with wall surfaces that are tapered relative to a lengthwise axis of the elongated nipple.

The needle 110 can extend from a distal end of the needle hub 102 and pass through the interior cavity 92 of the catheter hub 101 through the tapered seat 55 and the elongated seat 60 of the bushing 50 and into the catheter tube 140 with the needle tip 112 extending out a distal end 142 of the catheter tube 140 in the ready to use position. The distal portion of the catheter tube 140 can be tapered inwardly or have an opening that has a size smaller than an outer diameter of the needle 110 to form a seal around the opening of the catheter tube 140 with the needle 110 to prevent fluid from entering the space between the catheter tube 140 and the needle 110 when the needle tip 112 pierces the skin of a patient at an incision or insertion point. The space between the needle 110 and the interior of the catheter tube 140 can be annular or can be sectioned by baffles, such as ridges.

Blood flowing into the needle lumen to the needle hub 102 when piercing the skin, such as when entering a vein, is known as primary blood flashback. Blood entering the needle hub 102 can be collected in a vent plug or a blood collection device 107 for sampling. Retraction of the needle tip 112 in a proximal direction into the catheter tube 140 can allow fluid or blood to flow into the space between the needle 110 and the interior of the catheter tube 140, known as secondary blood flashback.

Figure 2:
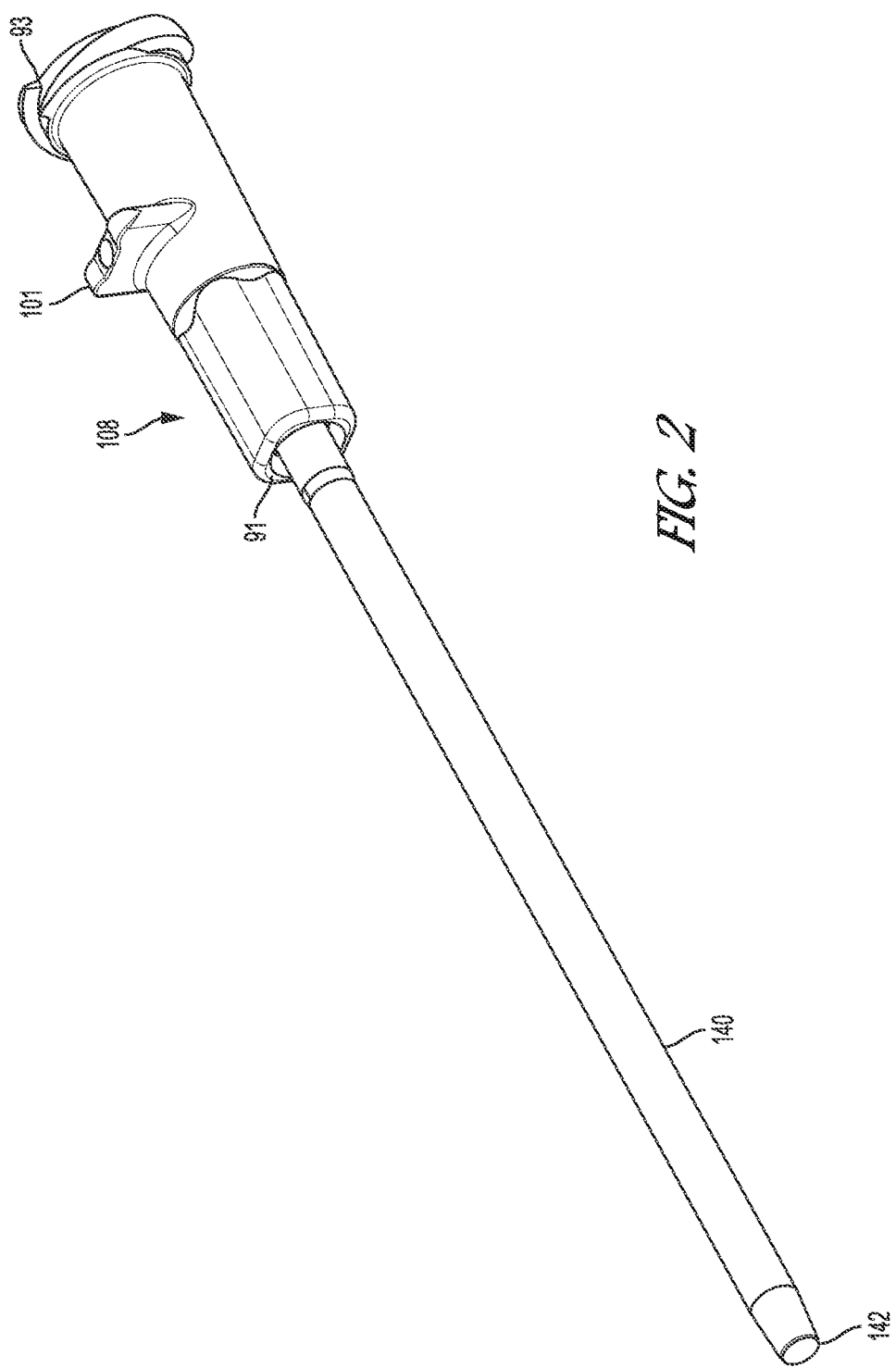
FIG. 2 is an isometric view of a catheter hub assembly provided in accordance with aspects of the present disclosure.
Figure 3:
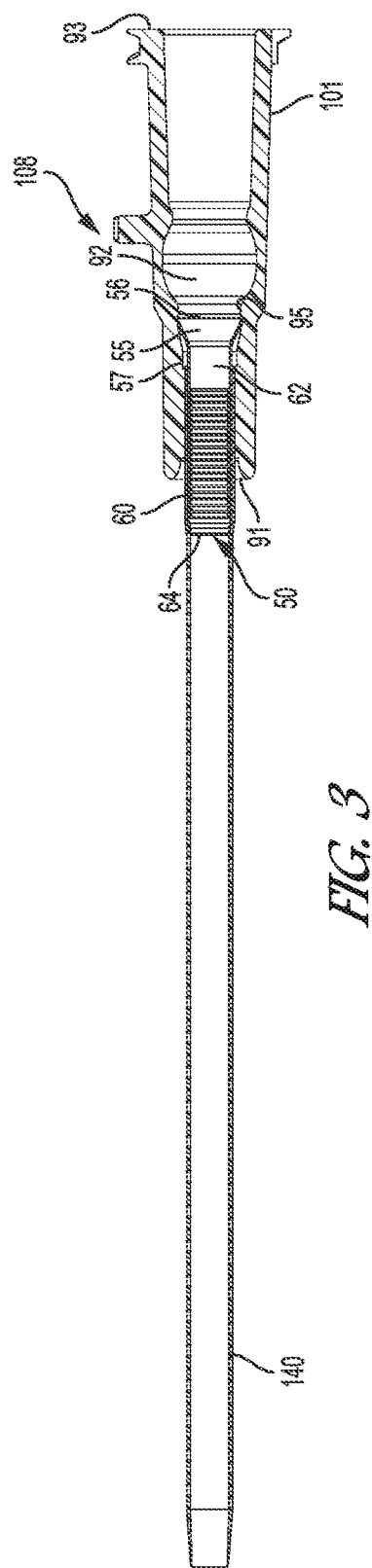
FIG. 3 is cross sectional view of the catheter hub assembly of FIG. 2.

FIG. 2 is an isometric of a catheter hub assembly 108 provided in accordance with an aspect of the present disclosure. The catheter hub assembly 108 can include a catheter hub 101, a catheter tube 140, and a bushing 50 located in the interior of the catheter hub. FIG. 3 is a cross-sectional view of the catheter hub assembly 108 of FIG. 2, which more clearly shows the bushing 50 located inside the interior cavity 92 with part of the elongated seat 60 extending distally out the distal end of the catheter hub 101. In an example, the part of the elongated seat 60 that extends out the distal end of the catheter hub is flexible, such as capable of bending or bowing.

With continued reference to FIG. 3, the catheter hub 101 has an interior cavity 92 defined between an opening at a proximal end 93 of the catheter hub 101 and an opening at a distal end 91 of the catheter hub 101. The bushing 50 can be inserted through the opening at the proximal end 93 of the catheter hub 101 and secured at a distal end of the interior cavity 92 of the catheter hub 101 via press fit, interference fit, adhesive, or combinations thereof. The bushing 50 may also be secured by other fastening means.

The bushing 50 can include a tapered seat 55 and an elongated seat 60 extending from the tapered seat 55. The tapered seat 55 and the elongated seat 60 can be integrally formed. Alternatively, the tapered seat 55 and the elongated seat 60 may be formed as separate pieces that are assembled together by welding or other fastening means. The choice of material of the bushing 50 is of the type that can withstand temperature fluctuations, impacts, corrosive substances, heat, and the atmosphere. In one example, the bushing 50 is metallic. In another example, the bushing 50 is plastic. A hydrophobic coating can be applied to at least portions of the inner and outer surfaces of the bushing 50 to prevent thrombus formation, phlebitis, or blood clots. In one example, a parylene coating is applied to at least the inside surface of the elongated seat portion to prevent thrombus formation. In still other examples, the bushing can be made from a polymer material or a polymer matrix material, such as medical grade silicone rubber.

The tapered seat 55 can be conical or funnel shaped having a defined thickness with a body having a wider opening at a proximal end 56 and a relatively narrower opening at the distal end 57 of the funnel body. The narrower opening transitions to the elongated seat 60. The tapered seat 60 can be rigid and inflexible or semi-rigid to maintain its conical shape after insertion into the catheter hub 101 to thereby wedge the proximal end of the catheter tube 140 to the interior of the catheter hub 101. Alternatively, the tapered seat 55 can be flexible and elastic and the catheter tube can be secured to the interior of the bushing 50. As indicated by the cross-sectional views of FIG. 3 and FIG. 5, the uniform dashed lines used for the catheter tube 140 indicate that the catheter tube 140 is monolithically formed from a single material. The catheter tube being monolithically formed from a single material is also understood by a skilled artisan as being singularly formed from the single material.

As discussed above, the tapered seat 55 can be secured inside the interior cavity 92 of the catheter hub by interference fit or other fastening means. A retaining mechanism or retainer 95 may also be provided inside the catheter hub 101 to secure the tapered seat 55 inside the interior cavity 92. For example, the retainer 95 can be a raised circumferential ring formed inside the interior cavity 92 of the catheter hub 101, thus forming a shoulder for the proximal end of the tapered seat 55 to rest against.

The bushing 50 can be inserted into the interior cavity 92 of the catheter hub 101 from the opening at the proximal end 93 of the catheter hub 101 and pushed distally until the tapered seat 55 slides over the retainer 95 and snaps into a securing position between the distal end 91 of the catheter hub 101 and the retainer 95. The raised circumferential ring or shoulder of the retainer 95 can have a bore diameter smaller or slightly smaller than a diameter of the wider opening at the proximal end 56 of the tapered seat 55 to provide a positive engagement for the tapered seat and prevent the tapered seat 55 of the bushing from sliding proximally out after snapping into position. The circumferential ring can taper gradually inward distally to assist sliding the bushing 50 into the securing position. The circumferential ring can also have a recess or other surface features to resist the distal end 57 of the tapered seat 55 and prevent the bushing 50 from sliding proximally out the interior cavity 92. In other examples, the retainer 95 may be a series of bumps or protrusions or a separately formed element that is inserted into and secured to the catheter hub after installation of the bushing.

FIG. 4 shows a side view of a bushing 50 provided in accordance with aspects of the present disclosure. As shown, the elongated seat 60 of the bushing 50 can be cylindrical and extends from the narrow opening at the distal end 57 of the tapered seat 55. The elongated seat 60 can have a smooth portion 62 transitioning from the distal end 57 of the tapered seat 55, a less smooth portion 63, and a distal end 68, which can have a smooth portion 64 with a taper as shown or can have a roughened surface. In an example, the smooth portion 62 at the proximal end of the elongated seat 60 has an exterior surface appearance that is generally flat or has fewer surface roughness than the less smooth portion 63. The less smooth portion 63 can be a flexible portion formed distally of the smooth portion 62 of the elongated seat 60. Optionally, the smooth portion 62 can be omitted, in which case, the elongated seat 60 includes only the less smooth portion 63 extending from the tapered seat 55. The smooth portion 62 and the tapered seat 55 can be rigid and inflexible or semi-rigid with some flexibility.

In an example, the less smooth or flexible portion 63 can be deformed or bend more readily than the smooth portion 62 at the proximal end, if incorporated. The flexible portion 63 is flexible and can bend along a length of the flexible portion 63 to form a bend, a curve, or a bow 67 along the length of the flexible portion 63, as further discussed below with reference to FIGS. 6 and 7. In another example, the flexible portion 63 can be compressed to form a shorter flexible portion 63, or pulled, such as stretch, to form a longer flexible portion 63.

FIGS. 4-8 illustrate the flexible portion 63 as having a number of alternating ridges 65 and grooves 66. The smooth portion 62 of the elongated seat 60, if incorporated, can be without any alternating grooves and ridges. The alternating ridges 65 and grooves 66 of the flexible portion can be rounded along the peaks and valleys to form a corrugated tube structure with a corrugated profile. In other examples, the alternating ridges 65 and grooves 66 may be folded upon each other to form an accordion like structure. In other embodiments, a combination of folded and rounded ridges and grooves can form the flexible portion 63. The corrugated tube structure allows the elongated seat 60 to move, flex, bow, and/or bend to adjust the flexible portion 63 for alignment, for use when a catheter tube is inserted into a patient, for securement, or any number of reasons. The corrugated structure can also absorb movement and vibration. Particularly, the alternating ridges 65 and grooves 66 allow the flexible portion 63 to bend and form one or more curves or bows 67 along the length of the flexible portion 63.

The flexible portion 63 of the elongated seat 60 can be manipulated from an initial straight configuration to a new configuration with one or more bends, with compressed portions, and/or stretched portions. In one embodiment, the new configuration can remain in its current modified configuration without elastically returning back to its original configuration. In another embodiment, the flexible portion 63 can be elastic, in which the flexible portion 63 springs back or returns to its original shape after the deformation. In yet other embodiments, the flexible portion 63 is allowed to be freely manipulated but can neither maintain the new configuration nor return to its original shape. Instead, the flexible portion 63 merely serves to prevent the catheter tube 140 from kinking or collapsing.

The corrugated tube structure can convey liquids and gases under pressure in the operating conditions of the catheter assembly 100. A hydrophobic coating can be applied to the bushing 50 to form a surface layer on the inside of the elongated seat 60 to repel blood and prevent thrombus formation or blood clotting from blood collecting on the corrugated profile surface.

The elongated seat 60 can be inserted into the catheter tube 140 so that the flexible portion 63 is inside the catheter tube and the proximal end of the catheter tube is located at the smooth portion 62. The catheter tube 140 can extend to the tapered seat 55, or at least part of the way thereof. In other examples, the catheter tube can extend to the intersection between the tapered seat 55 and the elongated seat 60, or just short of the intersection. The distal end, or insertion end 68 of the elongated seat 60 may be tapered and may be provided at a free end of the flexible portion 63 to aid assembling of the elongated seat 60 into the catheter tube.

A seal can form at the interface between the lumen 141 of the catheter tube 140 and the bushing 50 such that fluid cannot flow therebetween. A diameter of the elongated seat 60 can be the same or larger than the diameter of the lumen 141 of the catheter tube 140. Thus, the catheter tube 140 can be stretched over the elongated seat 60 to form a tight secure fit. Adhesive or other fixing means can be provided to further secure the catheter tube 140 to the elongated seat 60 and/or tapered seat 55.

With reference to FIG. 5, an alternative embodiment includes placing the catheter tube 140 inside the elongated seat 60 and then securing the catheter tube to the bushing. In an example, the bushing is made from a metal material or from a polymer or polymer matrix material. The catheter tube 140 can be inserted into the distal opening at the distal end 68 of the elongated seat 60. In an example, the proximal end of the catheter tube 140 is inserted to a location along the less smooth portion 63 of the elongated seat. In another example, the proximal end of the catheter tube 140 is inserted to a location along the smooth portion 62 of the elongated seat 60. Ultrasonic welding is then used to weld the catheter to the bushing using a modified sonotrode, which is understood to be a tool that creates ultrasonic vibrations.

With further reference to FIG. 5, another alternative embodiment includes placing the catheter tube 140 inside the elongated seat 60 and then securing the catheter tube to the bushing by adhesive or gluing. In an example, glue is applied, such as sprayed, dipped, or coated onto the inner surface of the elongated seat 60. The proximal end of the catheter tube 140 is then inserted into the distal opening at the distal end 68 of the elongated seat. The adhesive or glue may be air dried or dried with the aid of heat activation. Thus, as described, the catheter tube can be sleeved over the bushing or into the bushing. For example, the catheter tube can be sleeved over the elongated seat 60 or into the elongated seat 60.

Figure 6:
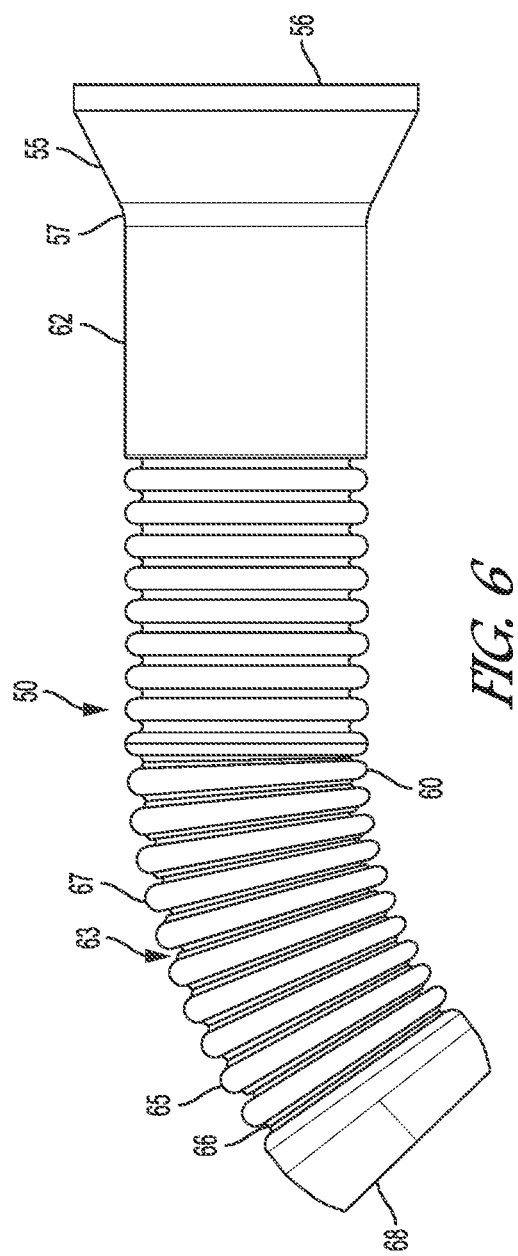
FIG. 6 shows the flex bushing of FIG. 4 with the catheter tube in a partially deflected state.

Referring to FIG. 6, the flexible portion 63 can bend to form an elbow 67, of small, intermediate, or large radius. The elbow, curve, bend, and bow can be understood as being a synonymous structure, which is a structure that is not substantially linear, as in a bushing with a straight or linear nose section. If the flexible portion 63 is long enough, more than one elbow 67 can form, such as a serpentine shape or configuration. The elbow 67 can form when one of the corrugated surfaces, such as the inside radius of the elongated seat, is shortened while the opposite surface, such as the outside radius of the elongated seat, is extended. A bend radius of the elbow 67 can depend on the diameter of the flexible portion 63 and the geometry and size of the ridges 65 and grooves 66, such as for example, the width of the ridges 65 and the width of the grooves 66, which can determine the number of ridges and grooves for a given length of the flexible portion or less smooth portion 64. The smallest bend radius of the elbow 67 can occur when the ridges 65 are contacting each other along the interior of the elbow 67 and farthest away from each other along the exterior of the elbow 67. Thus, the maximum bend angle of the bushing can be realized at the smallest bend radius of the elbow 67.

A bend radius of the at least one curve can define an elbow 67. The radial curve of the elbow 67 can depend on the diameter of the flexible portion and the geometry and size of the ridges and grooves of the flexible portion. For example, the width of the ridges and the width of the grooves along a length of a flexible portion can determine the number of ridges and grooves for the given length of the flexible portion. The smallest bend radius of the elbow can occur when the ridges are contacting each other along the interior of the elbow and farthest away from each other along the exterior of the elbow at the surface of the elbow.

If an imaginary plane bisects the diameter of the elongated seat of the bushing along the lengthwise direction of the bushing to divide the bushing into two halves, which can be called a first bushing half and a second bushing half, then the smallest bend radius of the elbow can occur when the ridges are contacting each other, or the gaps or spacing can shortened but not touch, along the interior of the first bushing half and farthest or further away from each other along the exterior of the second bushing half. In terms of the surfaces of the elongated seat, a first surface of the first bushing half can shorten and a second surface of the second bushing half can extend or lengthen when the at least one curve is formed on the bushing.

The reference to first bushing half and second bushing half are to distinguish between two sections of the elongate seat only but not structurally limiting. Thus, it can also be said then that the largest bend radius of the elbow can occur when the ridges are extended from each other along the exterior of the first bushing half and shortened or being closer together along the interior of the second bushing half. Said another way, the at least one curve can have a minimum bend radius when a first surface of the first bushing half of the elongated seat is extended and a second surface of the second bushing half of the elongated seat is shortened.

As the flexible portion of the bushing can bend in any number of locations and bending directions depending on the force applied to the catheter tube and/or the bushing to cause the bending and to cause at least one curve on the bushing, different opposed surfaces of the bushing can undergo changes, such as deformation, stretching, compressing, etc., to result in different parts of the bushing being called a first bushing half and a second bushing half depending on the direction of the bend.

Figure 7:
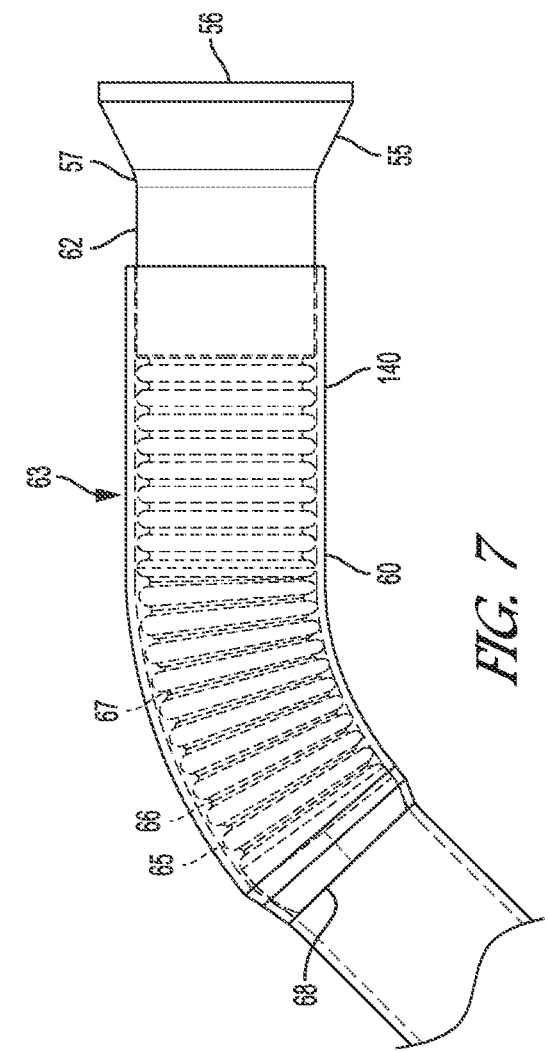
FIG. 7 shows the flex bushing of FIG. 4 with the catheter tube in a partially deflected state.

FIG. 7 shows the catheter tube 140 attached to the elongated seat 60 of the bushing 50. The catheter tube 140 can be sleeved onto the elongated seat 60 to surround at least the flexible portion 63 of the elongated seat 60 to prevent the catheter tube from kinking or collapsing within the flexible portion 63. The catheter tube 140 may also sleeve over the smooth portion 62 if the smooth portion 62 is present. The catheter tube 140 can bend with the elbow 67 along the flexible portion 63 to prevent the catheter tube 140 from kinking, collapsing, or restricting flow even if the catheter tube bends, such as during securement of the catheter assembly, due to inadvertent movement, etc. Thus, the flexible portion 63 can impart flexibility on the catheter tube 140 while maintaining flow through the catheter tube 140 and catheter hub 101. In an example, the flexible portion 63 can impart flexibility to the catheter tube 140 and prevents kinking to the catheter tube at a location externally of the catheter hub 101 while maintaining flow through the catheter tube 140 and catheter hub 101. The smooth portion 62 can be rigid and not bend.

The elbow 67 can also maintain the bent configuration of the catheter tube 140 by reducing or eliminating any restoration forces by a normally bent catheter tube 140. That is, any deviation of the catheter tube 140 from the axis of the catheter hub 101 can be imparted to the flexible portion 63 of the elongated seat 60 instead of the insertion point of the catheter tube to reduce patient discomfort. Furthermore, occurrence of phlebitis due to the movement of the catheter tube 140 at the insertion point can be reduced.

Figure 8:
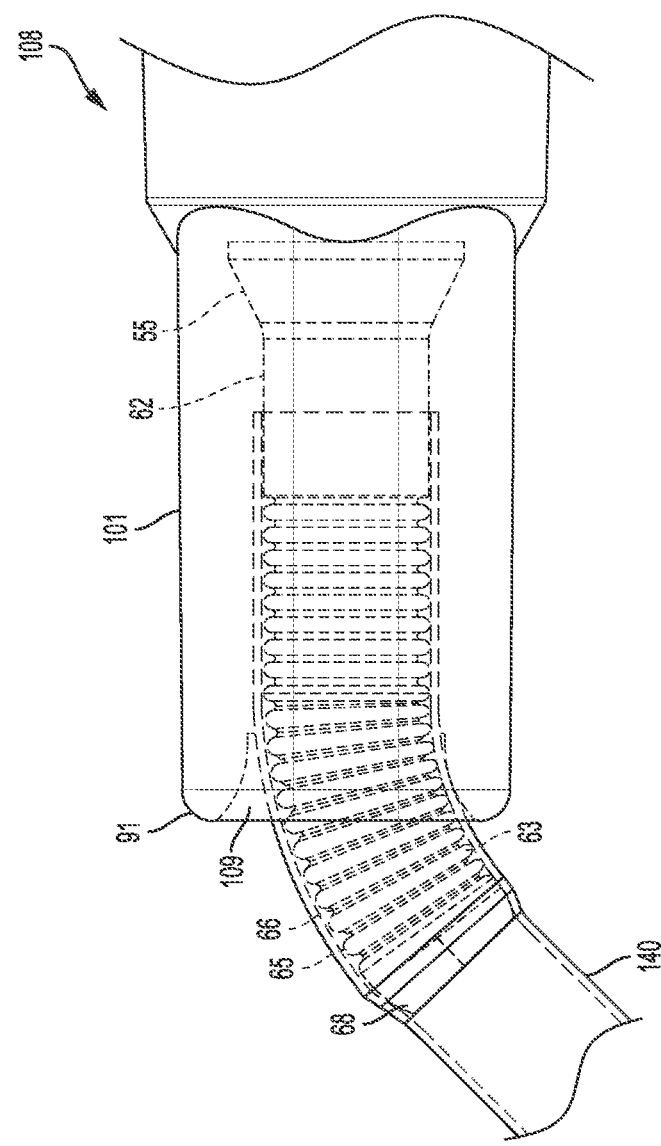
FIG. 8 shows the flex hub assembly of FIG. 2 in a partially deflected state.

Referring now to FIG. 8, a partial sectional view of the catheter hub assembly 108 of FIG. 2 is shown. In the view shown, the distal end 91 of the catheter hub 101 can have a radiused opening forming a recess 109 to accommodate flexing of the catheter tube 140 and the flexible portion 63 of the elongated seat at a location external of the catheter hub. The shape of the recess 109 is not limited and can embody any shape provided sufficient clearance is provided to accommodate movement of the catheter tube 140 and the flexible portion 63 at a location external of the catheter hub, such as distal of the distal end 91. The recess 109 may allow the catheter tube 140 to bend with the flexible portion 63 of the bushing 50 inside the recess 109. The recess 109 can be sized to restrict or allow the maximum bend of the flexible portion 63 with the catheter tube 140.

Figure 9A:
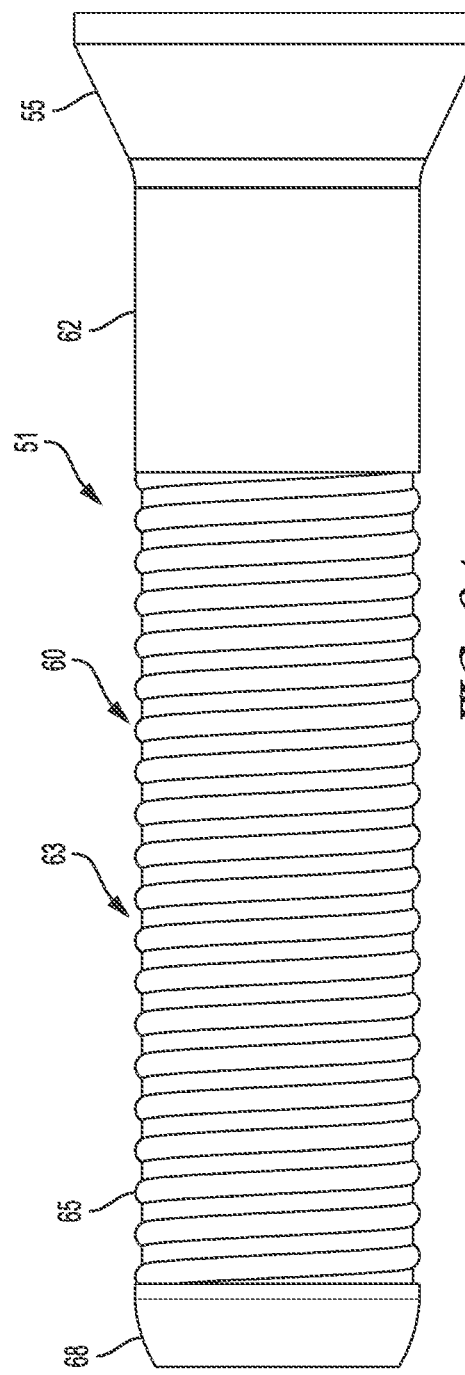
FIG. 9A shows another embodiment of a flex bushing provided in accordance with aspects of the present disclosure.

FIG. 9A illustrates another embodiment of a bushing 51 provided in accordance with aspects of the present disclosure. The bushing 51 of the present embodiment is similar to the bushing 50 embodied in FIGS. 4-8, except that a flexible portion 63 of the elongated seat 60 of the bushing 51 has a continuous ridge 65 spiraling continuously around the length of the flexible portion 63 from one end of the flexible portion 63 to the other end of the flexible portion 63 to form a spiral corrugated tube structure rather than alternating ridges 65 and grooves 66 along the length of the flexible portion 63. Thus, the present bushing 51 can be understood to include a helical shaped ridge 65 extending from one end of the flexible portion to another end of the flexible portion.

The bushing 51 can include a tapered seat 55 and an elongated seat 60 extending from the tapered seat 55. The elongated seat 60 can include the flexible portion 63 and an optional smooth portion 62 extending between the tapered seat 55 and the elongated seat 60. An insertion end 68 with a taper can be provided at the distal end of the flexible portion 63 to assist sleeving the catheter tube 140 over the elongated seat 60 of the bushing 51. A seal may also be formed between the lumen 141 of the catheter tube 140 and the bushing 51. The bushing 51 can also be bent along the flexible portion 63 to form one or more bends or elbows 67, similar to the bushing discussed above with reference to FIGS. 4-8. The bend radius of the elbow 67 can depend on the geometry and size of the continuous ridge 65 and the groove 66. When bending, a portion of one side of the flexible portion 63 will be shortened, and another portion at the opposite side will be extended.

Figure 9B:
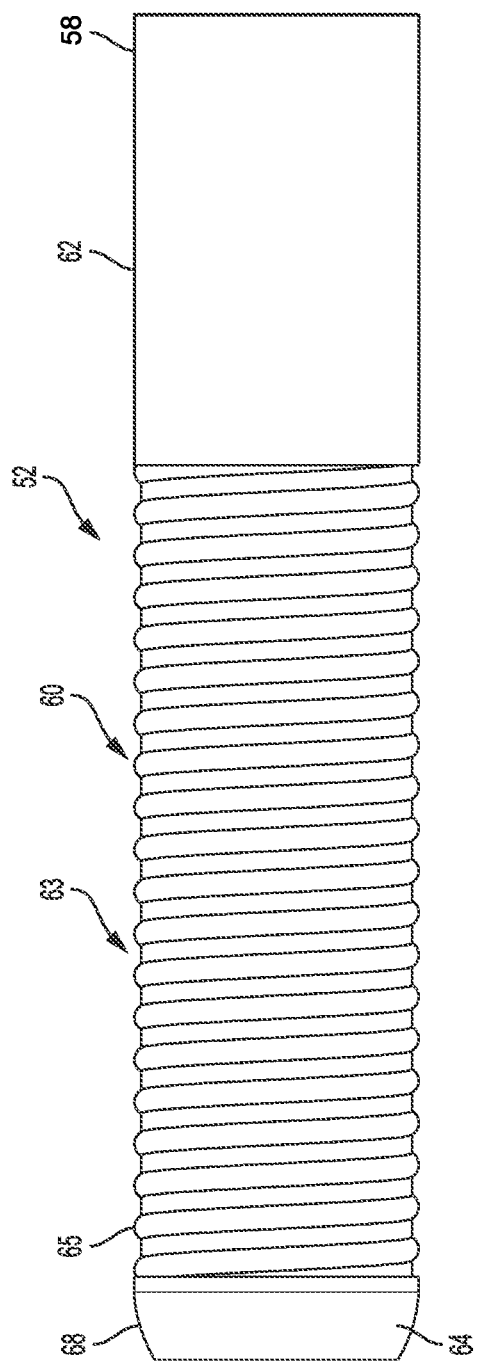
FIG. 9B shows yet another embodiment of a flex bushing provided in accordance with aspects of the present disclosure.

FIG. 9B illustrates yet another embodiment of a bushing 52 provided in accordance with aspects of the present disclosure. The bushing 52 of the present embodiment is similar to the bushing 50 embodied in FIGS. 4-9A in that a flexible portion 63 of the elongated seat 60 or distal seat of the bushing 52 can have alternating ridges and grooves along the length of the flexible portion 63 to form a corrugated structure or a continuous ridge 65 spiraling continuously around the length of the flexible portion 63 from one end of the flexible portion 63 to the other end of the flexible portion 63 to form a spiral corrugated tube structure. Thus, the present bushing 52 can be understood to include a helical shaped ridge 65 extending from one end of the flexible portion to another end of the flexible portion or alternating ridges and grooves along the length of the flexible portion 63.

The bushing 52 can include a non-tapered seat 58 and an elongated seat 60 extending from the non-tapered seat 58. The non-tapered seat 58 can also be called a proximal seat. The elongated seat 60 can include the flexible portion 63 and an optional smooth portion 62 extending between the non-tapered seat 58 and the elongated seat 60. As shown, the non-tapered seat 58 can be cylindrical and have substantially the same diameter as the smooth portion 62, in which case the smooth portion 62 is the non-tapered seat 58. The bushing 52 can be secured inside the catheter hub 101 using glue, interference fit, or other securing means to prevent the bushing 52 from moving distally out the catheter hub 101 or into the catheter tube 140. Alternatively, the non-tapered seat 58 can have a different diameter, shape, or size than the smooth portion 62. An insertion end 68 with a taper can be provided at the distal end of the flexible portion 63 to assist sleeving the catheter tube 140 over the elongated seat 60 of the bushing 52. A seal may also be formed between the lumen 141 of the catheter tube 140 and the bushing 52. The bushing 52 can also be bent along the flexible portion 63 to form one or more bends or elbows 67, similar to the bushing discussed above with reference to FIGS. 4-8. The bend radius of the elbow 67 can depend on the geometry and size of the continuous ridge 65 and the groove 66. When bending, a portion of one side of the flexible portion 63 will be shortened, and another portion at the opposite side will be extended.

In an example, the proximal seat can include one or more slits to facilitate flexing and therefore assembly of the proximal seat into the catheter hub to secure the catheter tube to the catheter hub. The one or more slits can be spaced from one another. The one or more seats can be parallel to the lengthwise axis of the catheter hub.

The bushings 50, 51, or 52 described herein can be formed by applying a deep drawing process and then follow by a hydroforming process to produce the corrugated surface. A coating process can then be applied to bushing, such as to the inner surface of the bushing 50, 51, or 52.

FIG. 10 shows an embodiment of a catheter assembly 127 comprising a catheter hub 101 and a catheter tube 140 attached to one of the bushings 50, 51, or 52 described elsewhere herein so that at least part of the elongated seat 60 extends out a distal end of the catheter hub 101. The assembly 127 further comprises a needle hub 102 having a needle 110 extending through the catheter tube 140, a side fluid port 184, and a fluid adaptor (not shown) attached to the side fluid port 184 by a tubing 188, which is attached to the side fluid port 184 by a second bushing 50, 51, or 52. Part of the elongated seat 60 of the second bushing 50, 51, or 52 extends out from or externally of the side fluid port 184. The tubing 188 can have a lumen for fluid flow between the side fluid port 184 and the fluid adaptor, which can be a needleless female Luer adaptor.

As shown in FIG. 10, the second bushing has a non-tapered seat 58, which is cylindrical. To prevent the second bushing from being pulled out of the catheter hub 101, the second bushing can be secured to the catheter hub with glue, interference fit, or a combination thereof.

The two bushings 50, 51, or 52 used with the catheter assembly 127 can each form one or more bends or elbows along a flexible portion of the respective bushing 50, 51, or 52. The flexible portions 64 of the two bushings 50, 51, or 52 can bend at or within the catheter hub 101 or side fluid port 184, near the respective opening thereof, and at a location external to the catheter hub or the side fluid port. Portions of the tubing 188 and the catheter tube 140 sleeved on the flexible portion 63 of the respective bushing can also bend along the flexible portion 63.

The proximal end 93 of the catheter hub 101 can be equipped with a septum, a seal or a valve, which can prevent flow thereacross after removal of the needle 110 and the needle hub 102. A needle guard 103 as discussed above can be incorporated between the needle hub 102 and the catheter hub 101. The catheter hub 101 is shown with a pair of wings. The needle hub can alternatively have a wing that extends distally along a side of the catheter hub opposite the side fluid port 184, instead of the wing on that side.

A needle tip 112 of the needle 110 extends distally past a distal opening of the catheter tube 140. Once inserted into the patient, blood flow can be monitored through the catheter tube 140, from secondary flashback. After successful venipuncture, the needle 110 can be removed from the patient, such as by withdrawing the needle hub 102 in the proximal direction. Fluid can be infused through the fluid adaptor via the tubing 188 to the side port 184 and then to the catheter hub 101. Alternatively if the proximal end of the catheter hub 101 has a valve instead of a septum or a seal, then fluid can be infused through the valve and the catheter tube. A clamp (not shown) can also be used to clamp off the extension line between the side fluid port 184 and the fluid adapter.

Figure 11:
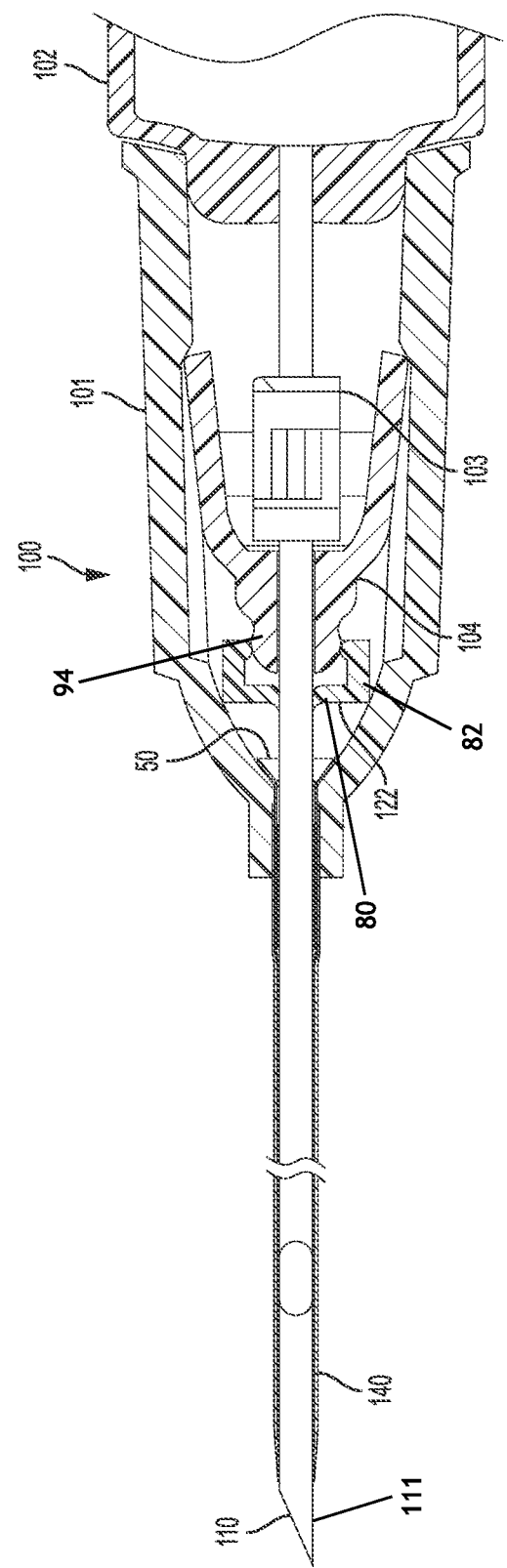
FIG. 11 shows a cross-sectional view of yet another embodiment of a safety IV catheter assembly.

Referring to FIG. 11, the catheter assembly 100 is similar to the catheter assembly of FIG. 1 except the catheter assembly can further include a valve activator or actuator 104 for opening a valve 122, which can have one or more slits defining a plurality of flaps that can be opened when the activator 104 is advanced by a male medical implement, such as a syringe tip, male Luer connector, or a Luer adaptor. The actuator 104 can have a nose section for physically opening the valve 122 and a plunger end comprising at least one plunger element or leg 90 configured to be pushed by a male medical implement. Optionally the valve 122, valve actuator 104, and needle guard 103 can be omitted. The valve 122 is housed within the interior cavity 92 of the catheter hub 101 and when incorporated has the needle 110 projecting therethrough in the ready position, such as shown in FIG. 11.

In some examples, three slits are provided on the valve 122 forming three flaps. In other examples, four slits in the shape of an "X" are provided to form four flaps. Different number of slits and flaps are contemplated. The valve 122 can be seated in a valve seat formed in the interior cavity 92 of the catheter hub. For example, an undercut can be formed in the interior of the catheter hub to retain the valve inside the interior cavity. In some examples, bumps or protrusions can be provided around an exterior of the valve to create paths between the valve and the interior of the catheter hub for venting during blood flashback. When the needle 110 is withdrawn from the catheter hub 101 after placement of the flexible tube 140 in the patient's vasculature, the one or more slit closes such that the valve 122 seals upon itself thereby restricting or limiting flow across the valve. The valve 122 thus restricts back bleed through the catheter hub 101. The valve 122 can be constructed of a material that forms a seal or a restriction at the interface with the needle 110 and reseals after the needle 110 is withdrawn. For example, and without limitation, the valve 122 can comprise silicone, silicone rubber, polypropylene, or other suitable materials. Unless indicated otherwise, the various components discussed elsewhere herein may be made from conventional materials.

The activator 104 can be provided to press against the valve 122, such as to project through the slits to open or deflect the flaps, when moved distally by a medical implement to open the valve 122 to allow fluid or solution to pass through the valve. The activator 104 has a passage formed through the nose section 94 for receiving the needle 110 in the ready position and for fluid flow when the catheter hub is connected to an IV line. The activator can have surface features to provide fluid mixing as fluid enters the catheter hub.

After the needle 110 and needle hub 102 are removed, a male medical implement, such as a Luer tip of a syringe, a male Luer connector or adaptor, such as used in connection with an IV line, a Luer access connector, or a vent plug, can be inserted to push the activator 104 distally into the valve 122 to open the seal. For example, the activator 104 can be advanced distally by a syringe tip, which presses against the proximal end of a disc 80 of the valve by the activator 104 to push a nose section 94 of the activator 104 distally forward into the valve 122 inside the skirt 82 to open the one or more slits. In an example, the activator 104 can have a wedge shaped nose section 94 to press open the valve 122 and an extension, plunger, or leg 90 extending in a proximal direction from the nose section to be pushed against by a male medical implement. Although a single extension or leg is usable to push the activator 104, two or more extensions are preferred. The extension 90 can embody one or more separate sections that can be pressed against by a male medical implement to advance the activator 104 against the valve 122. Two spaced apart extensions 90 can be provided to accommodate a needle guard therebetween. Examples of activators can be found in U.S. patent application Ser. No. 14/062,081, published as US 2014/0052065 A1, the contents of which are expressly incorporated herein by reference.

Figure 12:
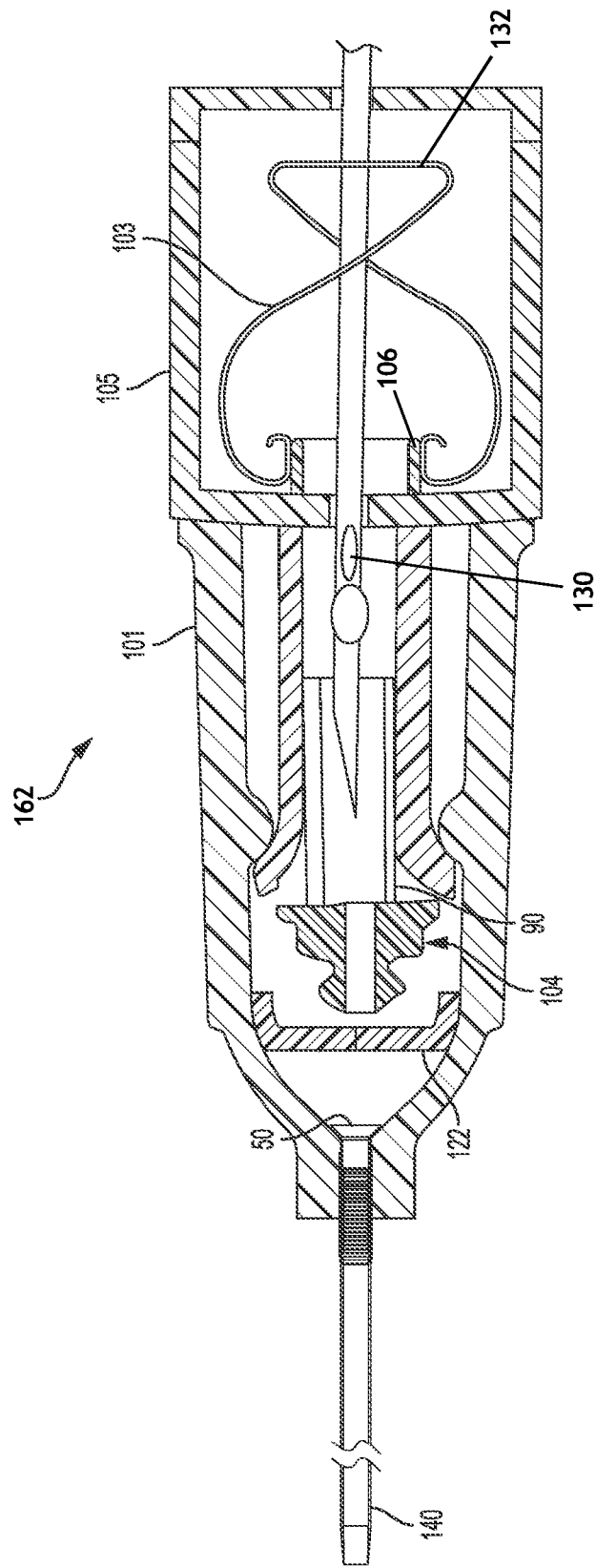
FIG. 12 shows a cross-sectional view of still yet another embodiment of a safety IV catheter assembly.

The valve 122 can also be modified or a different valve embodiment may be used with the present catheter assembly. For example, only the disc 80 and not a skirt 82 can be positioned in a seam of a two-piece catheter body. In yet another example, the needle shield 103 can be supported or housed in an intermediate hub between the catheter hub 101 and the needle hub 102, such as shown in FIG. 12. The intermediate hub can be removably coupled with the catheter hub 101 and may be referred to as a third hub or a needle shield or needle guard housing.

In still other examples, the catheter hub 101 is provided with a valve that can be actuated with fluid pressure only so that the actuator may be omitted from inside the interior cavity of the catheter hub. For example, the valve can flex with head pressure from an IV bag hung on an IV pole pushing up against the valve to open one or more flow paths or channels for fluid flow. In still other examples, the valve is positioned closed to the proximal opening of the catheter hub to be opened by a male Luer connected to the proximal open end of the catheter hub without the actuator or activator 104.

Part of the elongated seat of the bushing 50, 51, or 52 extending out a distal end of the catheter hub 101 can form one or more bends or elbows along a flexible portion of the bushing 50, 51, or 52. The flexible portion 63 can bend at, within the catheter hub 101, and/or external of the catheter hub. Portions of the catheter tube 140 sleeved on the flexible portion 63 can also bend along the flexible portion 63.

In FIG. 12, an exemplary safety catheter assembly 162 is shown, similar to the catheter device of FIG. 11 except that the needle safety shield 103, which comprises a biasing or resilient member, such as a resilient arm, is completely outside or substantially outside of the catheter hub 101. As shown, an intermediate hub, a needle shield hub, or a third hub 105 is located, at least in part, between the catheter hub 101 and the needle hub 102. The needle 110 has a change in profile 113, similar to other embodiments discussed elsewhere herein.

The needle shield 103 is located on or in the intermediate hub 105. The intermediate hub 105 can be enclosed as illustrated, can have a single wall, or can have openings in the wall. The needle shield 103 can be supported by a sleeve 106 of the intermediate hub 105 or can have the distal arms directly touching the needle 110. The sleeve 106 extends from a distal wall of the intermediate hub 105 so that the resilient arms of the needle safety shield 103 are supported on the sleeve 106. Alternatively, the needle 110 can incorporate a change in profile associated with a flashback indicator 130 or on a cover applied over the flashback indicator 130, such as a projection, for engaging an opening on the proximal wall of the needle shield 103. In use, as the needle 110 is retracted, the change in contour or profile 113 will engage the proximal wall 132 of the needle shield 103 and pull the needle shield 103 proximally so that the two resilient arms are pulled off the sleeve 106 or no longer biasing against the needle 110 and can overlap to block the needle tip 112.

The bushing 50, 51, or 52 extending out a distal end of the catheter hub 101 can form one or more bends or elbows along a flexible portion of the bushing 50, 51, or 52. The flexible portion 63 can bend at, within the catheter hub 101, or external of the catheter hub. Portions of the catheter tube 140 sleeved on the flexible portion 63 can also bend along the flexible portion 63.

Methods of making and of using the needle devices and their components as discussed elsewhere herein are contemplated.

Although limited embodiments of various catheter assemblies with a bushing have been specifically described and illustrated herein, many modifications and variations will be apparent to those skilled in the art. For example, any over the needle catheter can benefit by using the bushing disclosed herein to ensure the flow rate is not diminished through the catheter tube, flexibility for the patient to move about without causing further discomfort at or near the insertion point. Furthermore, it is understood and contemplated that features specifically discussed for one catheter assembly with a bushing may be adopted for inclusion with another catheter device provided the functions are compatible. Accordingly, it is to be understood that the catheter devices with a bushing and their components constructed according to principles of the disclosed devices, systems, and methods may be embodied other than as specifically described herein. The disclosure is also defined in the following aspects:

Aspect 1. A catheter assembly comprising:
- a catheter hub having a hub body defining an interior cavity;
- a bushing disposed in the interior cavity and having an elongated seat having a portion extending out a distal end of the catheter hub;
- a catheter tube sleeved over the elongated seat including over the portion that extends out the distal end;
- a needle hub with a needle comprising a needle shaft having a needle lumen and a needle tip, the needle shaft projecting through the elongated seat of the bushing and the catheter tube in a ready to use position; and
- wherein the elongated seat is bendable to form at least one curve along a length thereof to prevent kinking in the catheter tube, the at least one curve having a minimum bend radius when a first surface of the elongated seat is extended and a second surface opposite the first surface of the elongated seat is shortened.

Aspect 2. The catheter assembly of aspect 1, wherein the elongated seat comprises a plurality of alternating ridges and grooves.

Aspect 3. The catheter assembly of aspect 2, wherein the alternating ridges and grooves are folded upon each other to form an accordion structure.

Aspect 4. The catheter assembly of aspect 2, wherein the minimum bend radius is achieved when alternating ridges at a first surface of the elongated seat are extended further from each other and alternating ridges at a second surface opposite the first surface are closer together.

Aspect 5. The catheter assembly of aspect 2, wherein an inside surface of the elongated seat is provided with a hydrophobic coating.

Aspect 6. The catheter assembly of aspect 5, wherein the hydrophobic coating is a parylene coating layer.

Aspect 7. The catheter assembly of aspect 1, wherein the elongated seat forms a spiral corrugated tube structure having a continuous ridge spiraling continuously around the elongated seat along a length thereof.

Aspect 8. The catheter assembly of aspect 7, wherein the minimum bend radius is achieved when adjacent portions of the ridge at a first surface of the elongated seat are extended further from each other and adjacent portions of the ridge at a second surface opposite the first surface are closer together.

Aspect 9. The catheter assembly of aspect 7, an inside surface of the elongated seat is provided with a hydrophobic coating.

Aspect 10. The catheter assembly of aspect 9, wherein the hydrophobic coating is a parylene coating layer.

Aspect 11. The catheter assembly of aspect 1, wherein the bushing further comprises a tapered seat coupled to the elongated seat, the tapered seat being conical with a wider opening at a proximal end and a relatively narrower opening at a distal end.

Aspect 12. The catheter assembly of aspect 11, wherein the elongated seat comprises a smooth portion coupled to the tapered seat, the smooth portion extending from the distal end of the tapered seat and being more rigid than a portion of the elongated seat that is bendable.

Aspect 13. The catheter assembly of aspect 12, wherein a tapered portion extends from a distal end of the portion of the elongated seat that is bendable.

Aspect 14. The catheter assembly of aspect 11, wherein the tapered seat is integrally formed with the elongated seat.

Aspect 15. The catheter assembly of aspect 11, wherein the bushing is metallic.

Aspect 16. The catheter assembly of aspect 11, wherein a retainer is formed inside the interior cavity of the catheter hub to secure the tapered seat.

Aspect 17. The catheter assembly of aspect 16, wherein the retainer is a circumferential ring protruding from a surface of the interior cavity having a bore diameter smaller than a diameter of the tapered seat.

Aspect 18. The catheter assembly of aspect 1, wherein a recess is provided at the distal end of the catheter hub between the catheter tube and the catheter hub.

Aspect 19. The catheter assembly of aspect 18, wherein the recess is frustoconical shaped.

Aspect 20. The catheter assembly of aspect 1, further comprising a valve located in the interior cavity of the catheter hub.

Aspect 21. The catheter assembly of aspect 20, further comprising an activator located in the interior cavity of the catheter hub proximal of the valve, and wherein the activator is movable into the valve.

Aspect 22. The catheter assembly of aspect 21, wherein the activator comprises at least one plunger element configured to be pushed by a male Luer tip.

Aspect 23. The catheter assembly of aspect 1, further comprising a needle shield for covering the needle tip.

Aspect 24. The catheter assembly of aspect 23, wherein the needle shield is located substantially in the interior cavity of the catheter hub.

Aspect 25. The catheter assembly of aspect 23, wherein the needle shield is located in an intermediate hub proximal of the catheter hub.

Aspect 26. The catheter assembly of aspect 6, wherein a flashback indicator is provided with a protrusion for engaging the needle shield.

Aspect 27. The catheter assembly of aspect 23, further comprising a change in profile located proximally of the needle tip.

Aspect 28. The catheter assembly of aspect 1, further comprising a side port formed with the catheter hub and a second bushing having an elongated seat extending out a distal end of the side port.

Aspect 29. The catheter assembly of aspect 28, further comprising a tubing attached to the elongated seat of the second bushing at the side port.

Aspect 30. The catheter assembly of aspect 29, further comprising a fluid adaptor attached to the tubing.

Aspect 31. A method for manufacturing a catheter assembly, the method comprising:
  forming a catheter hub with an interior cavity;
  forming a bushing with a corrugated surface on an elongated seat;
  sleeving a catheter tube over the corrugated surface;
  securing the bushing in the interior cavity of the catheter hub;
  extending a portion of the corrugated surface out a distal end of the catheter hub;
  forming a needle hub with a needle comprising a needle shaft having a needle lumen and a needle tip, the needle shaft projecting through the elongated seat of the bushing and the catheter tube; and
  wherein the elongated seat is bendable to form at least one curve to prevent kinking in the catheter tube, the at least one curve having a minimum bend radius when a first surface of the elongated seat is extended and a second surface opposite the first surface of the elongated seat is shortened.

Aspect 32. The method of aspect 31, further comprising coating the inner surface of the elongated seat with a hydrophobic coating.

Aspect 33. The method of aspect 31, further comprising placing a needle guard having a proximal wall with a proximal opening and two resilient arms slidably on the needle shaft.

Aspect 34. The method of aspect 31, further comprising a valve for limiting fluid flow through a catheter hub.

Aspect 35. The method of aspect 31, further comprising an actuator in dynamic contact with the valve.

The disclosure is also defined in the following claims.

What is claimed is:

1. A catheter assembly comprising:
  a catheter hub having a hub body defining an interior cavity;
  a bushing disposed at least in part in the interior cavity, the bushing comprising a tapered seat and an elongated seat, the tapered seat having a proximal end that is wider than a distal end having the elongated seat extending therefrom, the elongated seat having a tubular structure defining a bore and having a portion extending out a distal end of the catheter hub, said elongated seat comprising a first bushing half and a second bushing half located on different sides of a plane extending lengthwise of a diameter of the bushing;

a catheter tube being formed from a single material and having an exterior surface and an interior surface defining a lumen that extends from a proximal opening at a proximal end to a distal opening at a distal end such that the exterior surface of the single material is at both the proximal opening and the distal opening, the catheter tube sleeved over the elongated seat of the bushing including over the portion that extends out the distal end of the catheter hub such that the interior surface at the proximal end of the catheter tube is directly pressed against an exterior of the bushing and the exterior surface at the proximal end of the catheter tube is directly pressed against an interior surface of the catheter hub;

a needle hub with a needle comprising a needle shaft having a needle lumen and a needle tip, the needle shaft projecting through the elongated seat of the bushing and out the distal opening at the distal end of the catheter tube in a ready to use position;

wherein the elongated seat is bendable to form at least one curve along a length thereof to prevent kinking in the catheter tube, the at least one curve having a minimum bend radius when a first surface of the first bushing half of the elongated seat is extended and a second surface of the second bushing half of the elongated seat is shortened.

2. The catheter assembly of claim 1, wherein the elongated seat comprises a plurality of alternating ridges and grooves at a distal end and a smooth portion at a proximal end, the smooth portion having a length extending in a proximal direction of an adjacent ridge.

3. The catheter assembly of claim 2, wherein the plurality of alternating ridges and grooves are folded upon each other to form an accordion structure.

4. The catheter assembly of claim 2, wherein the minimum bend radius is defined by the plurality of alternating ridges and grooves at the first surface of the first bushing half of the elongated seat extended further from each other and the plurality of alternating ridges and grooves at the second surface opposite the first surface being closer together.

5. The catheter assembly of claim 2, wherein the tapered seat has an outside diameter that is larger than a diameter of the plurality of alternating ridges and grooves.

6. The catheter assembly of claim 5, wherein a hydrophobic coating comprising a parylene coating layer is provided on an inside surface of the elongated seat.

7. The catheter assembly of claim 1, wherein an inside surface of the elongated seat is provided with a hydrophobic coating.

8. The catheter assembly of claim 7, wherein the hydrophobic coating is a parylene coating layer.

9. The catheter assembly of claim 1, wherein the elongated seat forms a spiral corrugated tube structure having a continuous ridge spiraling continuously around the elongated seat along a length thereof.

10. The catheter assembly of claim 9, wherein the minimum bend radius is defined by adjacent portions of the continuous ridge at the first surface of the first bushing half of the elongated seat extended further from each other and adjacent portions of the continuous ridge at the second surface opposite the first surface being closer together.

11. The catheter assembly of claim 1, wherein the elongated seat has a smooth tapered portion with an opening at a distal end.

12. The catheter assembly of claim 1, wherein the catheter tube is monolithically formed from the single material.

13. A method for manufacturing a catheter assembly, the method comprising:
forming a catheter hub with an interior cavity;
sleeving a catheter tube, which is formed from a single material and having an exterior surface and an interior surface defining a lumen that extends from a proximal opening to a distal opening such that the exterior surface of the single material is at both the proximal opening and the distal opening, over a corrugated surface on an elongated seat of a bushing, which is located distally of a conical seat, said elongated seat comprising a first bushing half and a second bushing half located on different sides of a plane extending lengthwise of the bushing, such that the interior surface at a proximal end of the catheter tube is directly pressed against an exterior of the bushing and the exterior surface at the proximal end of the catheter tube is pressed against an interior surface of the catheter hub;
securing the bushing in the interior cavity of the catheter hub by placing the conical seat against a tapered surface of the catheter hub;
extending a portion of the corrugated surface out a distal end of the catheter hub;
forming a needle hub with a needle comprising a needle shaft having a needle lumen and a needle tip, the needle shaft projecting through the elongated seat of the bushing and the catheter tube and extending out the distal opening at a distal end of the catheter tube; and
wherein the elongated seat is bendable to form at least one curve to prevent kinking of the catheter tube, the at least one curve having a minimum bend radius when a first surface of the first bushing half of the elongated seat is extended and a second surface of the second bushing half of the elongated seat is shortened.

14. The method of claim 13, further comprising coating an inner surface of the elongated seat with a hydrophobic coating.

15. The method of claim 13, further comprising placing a needle guard having a proximal wall with a proximal opening and two resilient arms slidably on the needle shaft.

16. The method of claim 13, further comprising a valve for limiting fluid flow through the catheter hub.

17. The method of claim 13, wherein the catheter tube is monolithically formed from the single material.

18. A catheter assembly comprising:
a catheter hub having a hub body defining an interior cavity;
a bushing disposed at least in part in the interior cavity, the bushing comprising a conical seat and an elongated seat having a portion extending out a distal end of the catheter hub, said elongated seat comprising a first bushing half and a second bushing half located on different sides of a plane extending lengthwise of a diameter of the bushing;
a catheter tube sleeved over the elongated seat including over the portion that extends out the distal end of the catheter hub, the catheter tube being formed from a single material and having an exterior surface that extends from a proximal end opening to a distal end opening at a distal end such that the exterior surface of the single material is at both the proximal end opening and the distal end opening and wherein the proximal end of the catheter tube is directly pressed between an exterior of the bushing and an interior surface of the catheter hub;

a needle hub with a needle comprising a needle shaft having a needle lumen and a needle tip, the needle shaft projecting through the elongated seat of the bushing and the needle tip extending beyond the distal end opening of the catheter tube in a ready to use position; and wherein the elongated seat comprises a plurality of alternating ridges and grooves located distally of a smooth portion and the elongated seat is bendable to form at least one curve along a length thereof to prevent kinking in the catheter tube, the at least one curve having a minimum bend radius when a first surface of the first bushing half of the elongated seat is extended and a second surface of the second bushing half of the elongated seat is shortened.

19. The catheter assembly of claim 18, wherein the plurality of alternating ridges and grooves extend less than a total length of the elongated seat.

20. The catheter assembly of claim 19, wherein the minimum bend radius is defined by the plurality of alternating ridges and grooves at the first surface of the first bushing half of the elongated seat extended further from each other and the plurality of alternating ridges and grooves at the second surface opposite the first surface being closer together.

21. The catheter assembly of claim 18, wherein the catheter tube is monolithically formed from the single material.

* * * * *